United States Patent
Ponnaluri et al.

(10) Patent No.: US 11,840,741 B2
(45) Date of Patent: *Dec. 12, 2023

(54) ANALYSIS OF CHROMATIN USING A NICKING ENZYME

(71) Applicant: New England Biolabs, Inc., Ipswich, MA (US)

(72) Inventors: Chaithanya Ponnaluri, Ipswich, MA (US); Hang-Gyeong Chin, Ipswich, MA (US); Pierre O. Esteve, Ipswich, MA (US); Sriharsa Pradhan, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 91 days.

This patent is subject to a terminal disclaimer.

(21) Appl. No.: 17/454,082

(22) Filed: Nov. 9, 2021

(65) Prior Publication Data

US 2022/0056537 A1 Feb. 24, 2022

Related U.S. Application Data

(62) Division of application No. 16/327,698, filed as application No. PCT/US2017/049556 on Aug. 31, 2017, now Pat. No. 11,198,910.

(Continued)

(51) Int. Cl.
*C12Q 1/68* (2018.01)
*C12Q 1/6886* (2018.01)
(Continued)

(52) U.S. Cl.
CPC ......... *C12Q 1/6886* (2013.01); *C12Q 1/6806* (2013.01); *C12Q 1/6827* (2013.01);
(Continued)

(58) Field of Classification Search
CPC ....................................................... C12Q 1/68
(Continued)

(56) References Cited

U.S. PATENT DOCUMENTS

| | | |
|---|---|---|
| 5,264,343 A | 11/1993 | Krystosek et al. |
| 5,981,179 A | 11/1999 | Lorinez et al. |

(Continued)

FOREIGN PATENT DOCUMENTS

| | | |
|---|---|---|
| EP | 0799897 A1 | 10/1997 |
| WO | 2006047183 A2 | 5/2006 |
| WO | 2011050147 A1 | 4/2011 |

OTHER PUBLICATIONS

Zaret, et al: Pioneer transcription factors, chromatin dynamics, and cell fate control. Curr Opin Genet Dev 2016, 37:76-81.

(Continued)

*Primary Examiner* — Aaron A Priest
(74) *Attorney, Agent, or Firm* — New England Biolabs, Inc

(57) ABSTRACT

Provided herein, among other things, are various compositions and methods for analyzing chromatin. In some embodiments, the composition may comprise a mixture of a nicking enzyme, four dNTPs, at least one labeled dNTP and, optionally, a polymerase. In some embodiments, this method may comprise: obtaining a sample comprising chromatin, reacting the sample with the composition to selectively label the open chromatin in the sample, and analyzing the labeled sample.

9 Claims, 20 Drawing Sheets

Specification includes a Sequence Listing.

Related U.S. Application Data

(60) Provisional application No. 62/383,151, filed on Sep. 2, 2016.

(51) Int. Cl.
    *C12Q 1/6806* (2018.01)
    *C12Q 1/6841* (2018.01)
    *C12Q 1/6869* (2018.01)
    *C12Q 1/6827* (2018.01)

(52) U.S. Cl.
    CPC ......... *C12Q 1/6841* (2013.01); *C12Q 1/6869* (2013.01); *C12Q 2521/301* (2013.01); *C12Q 2521/331* (2013.01); *C12Q 2525/117* (2013.01); *C12Q 2527/156* (2013.01); *C12Q 2531/119* (2013.01); *C12Q 2535/122* (2013.01); *C12Q 2543/10* (2013.01); *C12Q 2563/131* (2013.01); *C12Q 2565/133* (2013.01); *C12Q 2600/154* (2013.01)

(58) Field of Classification Search
    USPC ........................................................ 435/6.1
    See application file for complete search history.

(56) References Cited

U.S. PATENT DOCUMENTS

| | | | |
|---|---|---|---|
| 6,191,267 | B1 | 2/2001 | Kong et al. |
| 7,081,358 | B2 | 7/2006 | Teiter et al. |
| 7,943,303 | B2 | 5/2011 | Xu et al. |
| 8,163,529 | B2 | 4/2012 | Xu et al. |
| 10,221,436 | B2 * | 3/2019 | Hardenbol ............... C12P 19/34 |
| 10,851,406 | B2 * | 12/2020 | Maples ................... C07H 21/04 |
| 2005/0136462 | A1 | 6/2005 | Zhu et al. |
| 2010/0323912 | A1 * | 12/2010 | Korlach ................... G01N 33/68 435/6.16 |
| 2011/0306042 | A1 * | 12/2011 | Jouvenot ................... C12Q 1/68 435/6.1 |
| 2013/0130255 | A1 * | 5/2013 | Dedecker ............ G01N 21/6458 435/287.2 |
| 2016/0177380 | A1 * | 6/2016 | Ruan ..................... C12Q 1/6806 435/6.12 |

OTHER PUBLICATIONS

Weipoltshammer, et al: Morphology of nuclear transcription. Histochem Cell Biol 2016, 145:343-358.
Tsompana, et al: Chromatin accessibility: a window into the genome. Epigenetics Chromatin 2014, 7:33.
Radman-Livaja, et al: Nucleosome positioning: how is it established, and why does it matter? Dev Biol 2010, 339:258-266.
Boyle, et al: High-resolution genome wide in vivo footprinting of diverse transcription factors in human cells. Genome Res 2011, 21:456-464.
Schones, et al: Dynamic regulation of nucleosome positioning in the human genome. Cell 2008, 132:887-898.
Shivaswamy, et al: Dynamic remodeling of individual nucleosomes across a eukaryotic genome in response to transcriptional perturbation. PLoS Biol 2008, 6:e65.
Lee, et al: Evidence for nucleosome depletion at active regulatory regions genome-wide. Nat Genet 2004, 36:900-905.
Boeger: Nucleosomes unfold completely at a transcriptionally active promoter. Mol Cell 2003, 11:1587-1598.
Wallrath, et al: Architectural variations of inducible eukaryotic promoters: preset and remodeling chromatin structures. Bioessays 1994, 16:165-170.
Hogan, et al: Cell cycle-specified fluctuation of nucleosome occupancy at gene promoters. PLoS Genet 2006, 2:e158.
Korber, et al: Evidence for histone eviction in trans upon induction of the yeast PHO5 promoter. Mol Cell Biol 2004, 24:10965-10974.
Shu, et al: Genome-wide analysis of the relationships between DNase I HS, histone modifications and gene expression reveals distinct modes of chromatin domains. Nucleic Acids Res 2011, 39:7428-7443.
Buck, et al: A chromatin-mediated mechanism for specification of conditional transcription factor targets. Nat Genet 2006, 38:1446-1451.
Wu, et al: The chromatin structure of specific genes: II. Disruption of chromatin structure during gene activity. Cell 1979, 16:807-814.
Wu, The 5' ends of *Drosophila* heat shock genes in chromatin are hypersensitive to DNase I. Nature 1980, 286:854-860.
Keene, et al: Micrococcal nuclease as a probe of DNA sequence organization and chromatin structure. Cell 1981, 27:57-64.
Levy, et al: Chromatin fine structure of active and repressed genes. Nature 1981, 289:198-203.
Park, ChIP-seq: advantages and challenges of a maturing technology. Nat Rev Genet 2009, 10:669-680.
Jin, et al: Genome-wide detection of DNase I hypersensitive sites in single cells and FFPE tissue samples. Nature 2015, 528:142-146.
Nagy, at al: Genomewide demarcation of RNA polymerase II transcription units revealed by physical fractionation of chromatin. Proc Natl Acad Sci U S A 2003, 100:6364-6369.
Crawford, et al: Genome-wide mapping of DNase hypersensitive sites using massively parallel signature sequencing (MPSS). Genome Res 2006, 16:123-131.
Buenrostro, et al: Transposition of native chromatin for fast and sensitive epigenomic profiling of open chromatin, DNA-binding proteins and nucleosome position. Nat Methods 2013, 10:1213-1218.
Langmead, et al: Fast gapped-read alignment with Bowtie 2. Nat Methods 2012, 9:357-359.
Zhang, et al: Model-based analysis of ChIP-Seq (MACS). Genome Biol 2008, 9:R137.
Heinz, et al: Simple combinations of lineage-determining transcription factors prime cis-regulatory elements required for macrophage and B cell identities. Mol Cell 2010, 38:576-589.
Kolde, pheatmap: Pretty Heatmaps. 2015.
Meyer, et al: Identifying and mitigating bias in next-generation sequencing methods for chromatin biology. Nat Rev Genet 2014, 15:709-721.
Ross-Innes, et al., Differential oestrogen receptor binding is associated with clinical outcome in breast cancer. Nature 2012, 481:389-393.
Robinson, Integrative Genomics Viewer, Nature Biotechnology 2011 29, 24-26.
Gutjahr, et al., Nucleic Acids Res. 42:e77 (2014).
Xu, et al., Sci. Rep. 6:28579 2016.
Bellamy, et al. J. Mol. Biol. 2005 345, 641-653.
Heiter, et al., J. Mol. Biol. 2005 348, 631-640.
Xu, et al., Proc. Natl. Acad. Sci. USA 2001 98, 12990-12995.
Samuelson, et al., Nucl. Acids Res. 2004 32, 3661-3671.
Zhu, et al., J. Mol. Biol. 2004 337, 573-583.
Morgan, et al., Biol. Chem. 2000 381, 1123-1125.
Chan, Nucl. Acids Res. 2004 32, 6187-6199.
Sasnauskas, Proc. Natl. Acad. Sci. USA 2003 100, 6410-6415.
Jo, et al., PNAS 2007 104:2673-2678.
Xiao, et al., Nucleic Acids Res. 2007 35:e16.
Hsu, et al., Nature Biotechnology 2013 31: 827-832.
Kolb, et al., Drug Discov Today 2003 8: 1128-113.
Baskin, et al., Proc. Natl. Acad. Sci. 2007 104: 16793-16797.
Brenner et al., Proc. Natl. Acad. Sci., 97: 1665-1670 (2000).
Shoemaker, et al, Nature Genetics, 14: 450-456 (1996).
Kricka, et al., Ann Clin Biochem. 39:114-29, 2002.
Margulies, et al., Nature 2005 437: 376-80.
Ronaghi, et al., Analytical Biochemistry 1996 242: 84-9.
Shendure, Science 2005 309: 1728.
Melfort, et al., Brief Bioinform. 2009 10:609-18.
Fox, et al., Methods Mol Biol. 2009; 553:79-108.
Appleby, et al., Methods Mol Biol. 2009;513:19-39.

(56) References Cited

OTHER PUBLICATIONS

English, PLoS One. 2012 7: e47768.
Morozova, Genomics. 2008 92:255-64.
Genbank accession No. AAU27318.1.
Luzzietti, et al.: Nature Protocol, 7, 4, 643-653, 2012.
Song, et al: Cold Spring Harbor Protoc, 2, 2010.

* cited by examiner

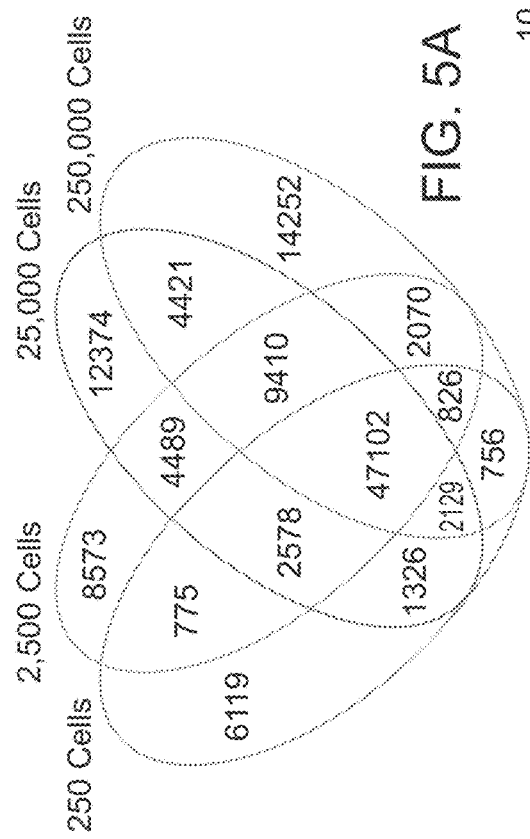
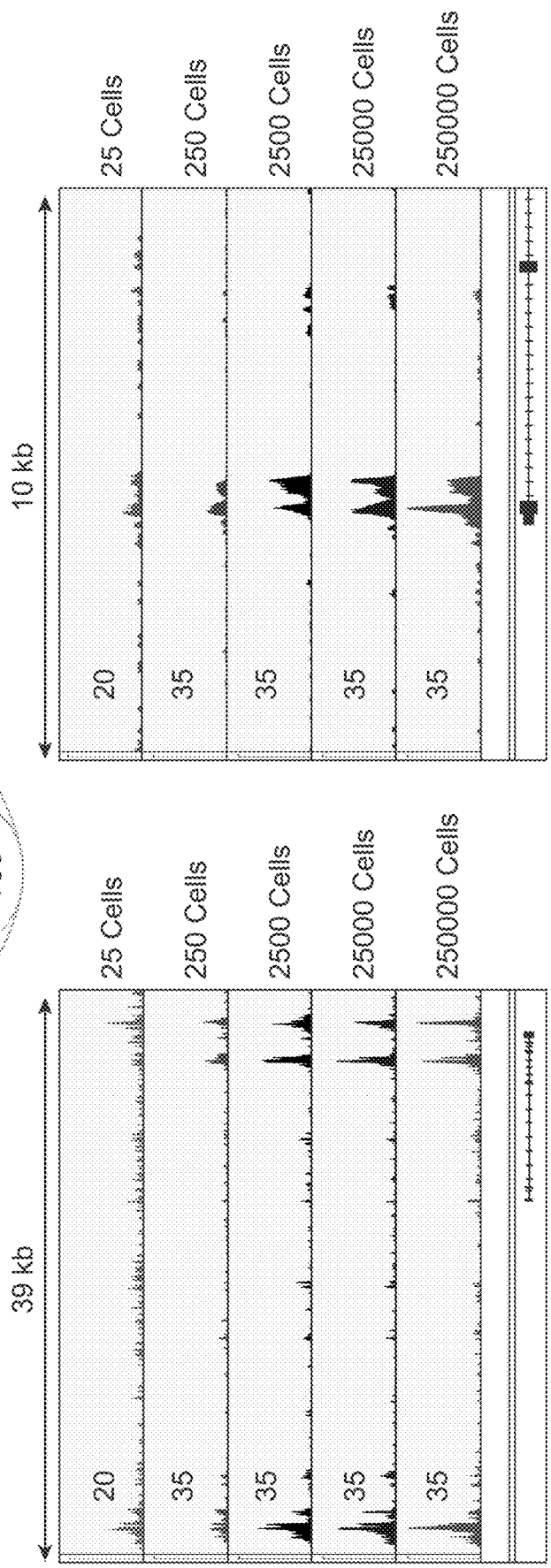

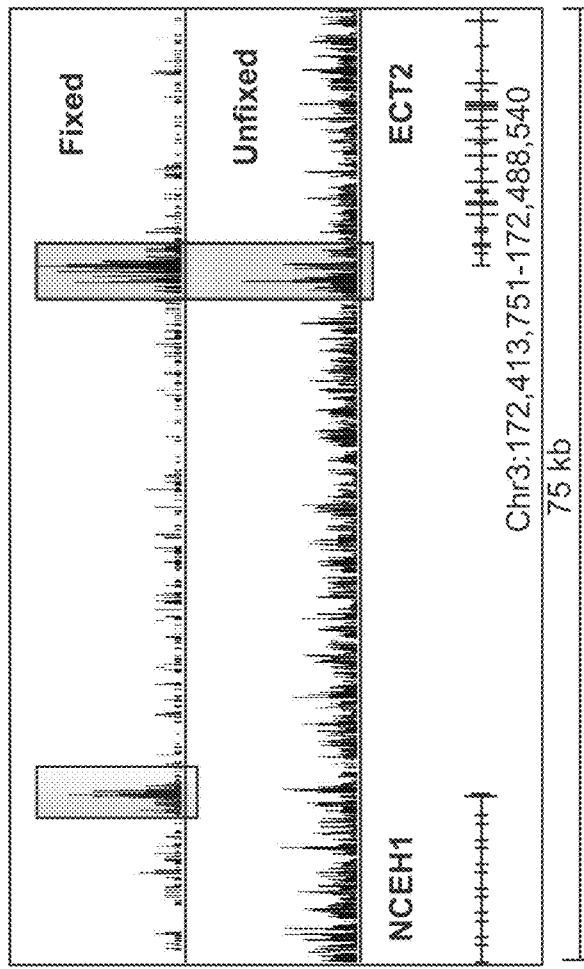
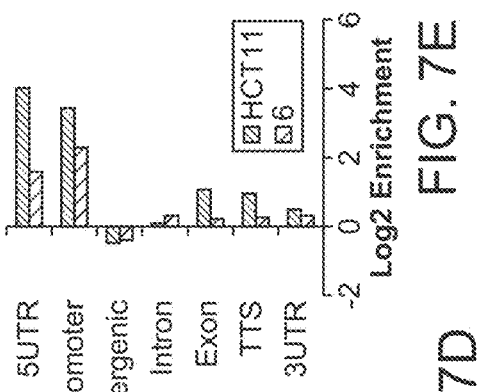
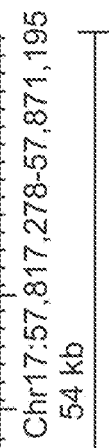
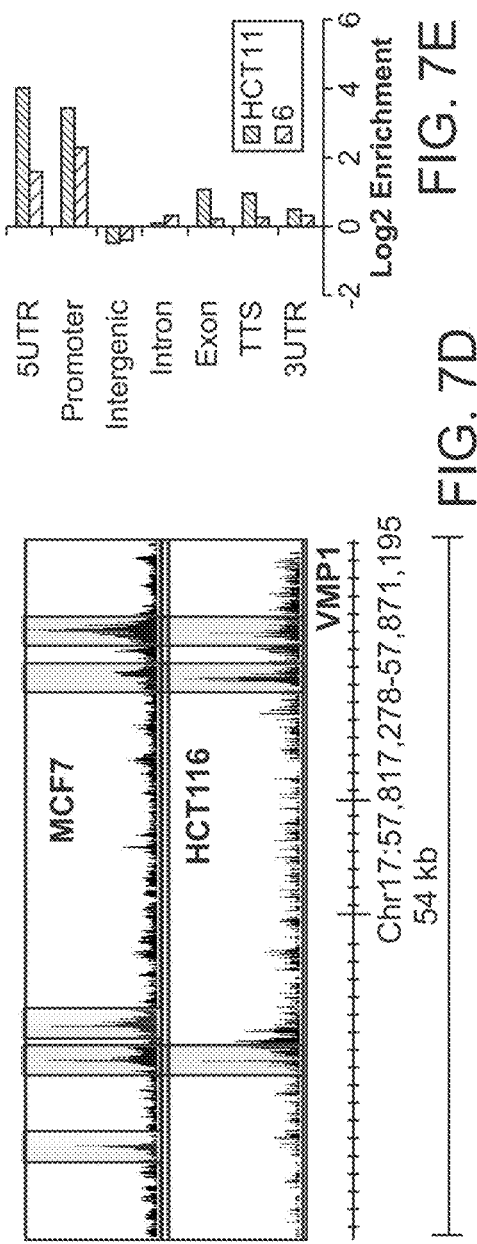
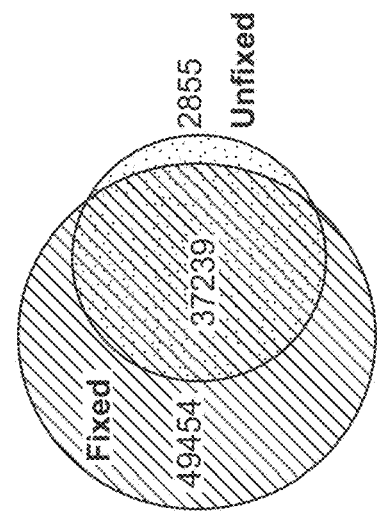
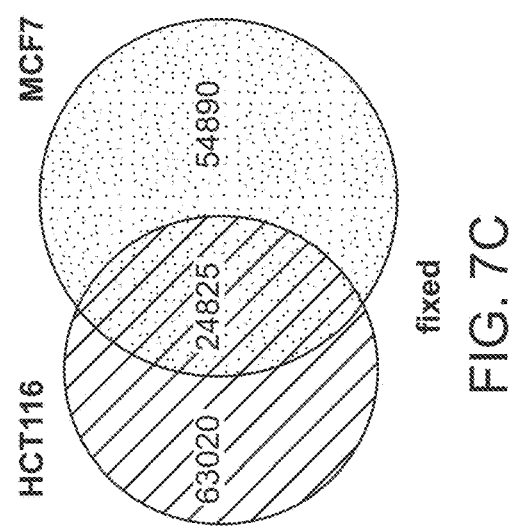
FIG. 7A  FIG. 7B  FIG. 7C  FIG. 7D  FIG. 7E

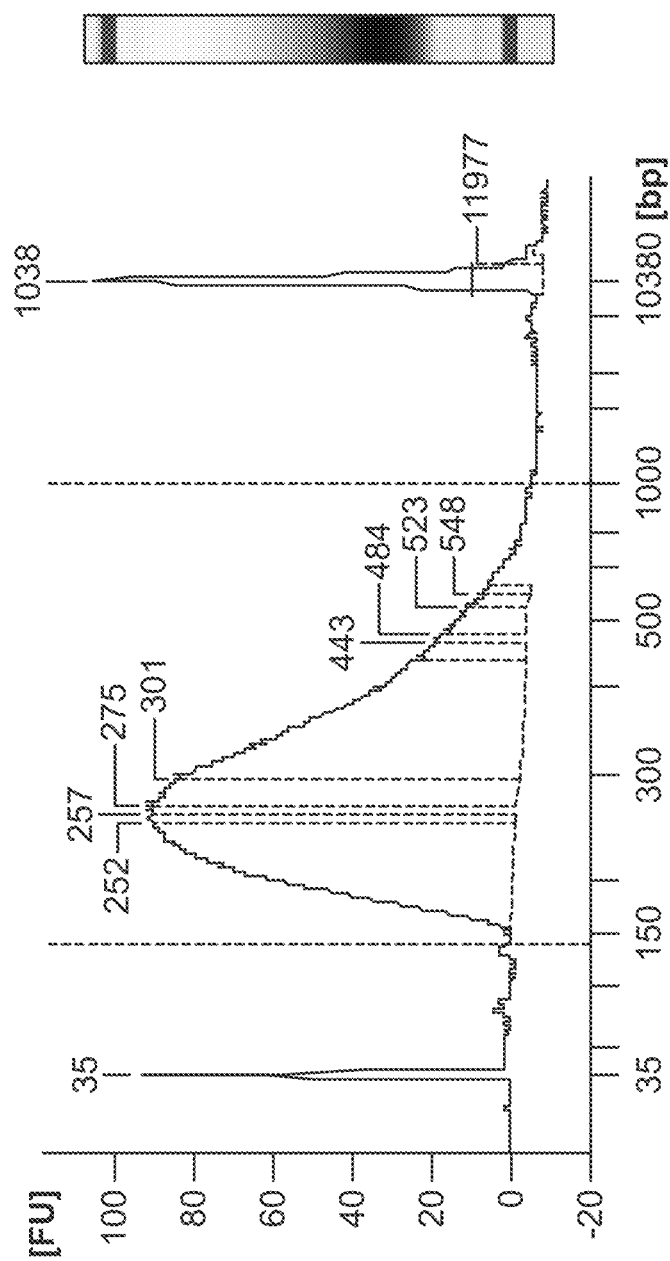
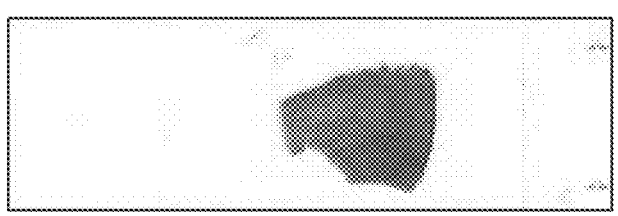
FIG. 15B
FIG. 15A

SEQUENCE LISTING

```
<160> NUMBER OF SEQ ID NOS: 4

<210> SEQ ID NO 1
<211> LENGTH: 399
<212> TYPE: PRT
<213> ORGANISM: Legionella pneumophila

<400> SEQUENCE: 1

Met Lys Ile Tyr Ser Phe Asp Thr Leu Ala Asn Ala Asp Leu Ile Ile
```

```
              1               5              10              15
            Asp Ala Val Tyr Glu Gly Gly Ser Ser Gly Asn Ala Ser Asp Asp Pro
                             20              25              30
            Ile Ser Lys Ile Ile Lys Gly Ile Gly Asn Met Gly Gly Phe Arg Ser
                             35              40              45
            Ala Gly Gln Gly Ile Phe Lys Lys Leu Ile Val Leu Tyr Thr Asn Met
                             50              55              60
            Glu Asp Gly Asp Trp Pro Asp Ser Ile Asp Thr Ser Lys Gly Gln Phe
             65              70              75              80
            Ile Tyr Tyr Gly Asp Asn Lys His Pro Gly His Asp Ile His Asp Thr
                             85              90              95
            Pro Arg Gln Gly Asn Ala Thr Leu Lys Met Leu Phe Asp Ser Thr His
                            100             105             110
            Asn Glu Lys Asp Ala Arg Arg Ile Val Pro Pro Ile Phe Ile Phe Val
                            115             120             125
            Lys Tyr Pro Thr Ala Ser Ser Ser Arg Ser Val Gln Phe Lys Gly Val
                            130             135             140
            Ala Val Pro Gly Tyr Pro Gly Leu Ser Ala Thr Asp Asp Leu Ile Ala
            145             150             155             160
            Val Trp Lys Thr Thr Asn Gly Gln Arg Phe Gln Asn Tyr Arg Ala Ile
                            165             170             175
            Phe Thr Ile Leu Asn Ile Pro Met Val Ser Arg Lys Trp Ile Asn Ser
                            180             185             190
            Leu Phe Asp Pro Phe Gly Gln Asp Asn Ser Leu Asn Pro Phe Tyr Gln
                            195             200             205
            Trp Lys Ile Ser Gly Lys Ala Asp Val Leu Ile Ala Pro Ser Thr Lys
                            210             215             220
            Thr Ile Arg Thr Gln Ile Glu Gln Met Pro Arg Thr Lys Leu Glu Arg
            225             230             235             240
            Glu Ile Leu Gln Ala Val Phe Asp Tyr Phe Cys Glu Ala Pro Ile Lys
                            245             250             255
            Phe Glu Ala Cys Ala Ala Lys Ile Phe Gln Leu Tyr Asp Glu Asn Val
                            260             265             270
            Leu Ile Asp Glu Ile Thr Arg Ser Ala Val Asp Gly Lys Asp Ala
                            275             280             285
            Ile Gly Arg Tyr Val Leu Gly Ile Lys Glu Asp Pro Val Tyr Ala Glu
                            290             295             300
            Phe Phe Leu Glu Ala Lys Cys Tyr Gln Pro Gly Leu Asn Gly Gln Asn
            305             310             315             320
            Ile Asn Ser Val Gly Val Lys Glu Val Ser Arg Leu Ile Ser Arg Ile
                            325             330             335
            Lys Asn Arg Gln Phe Gly Val Leu Val Thr Thr Ser Phe Ile Ala Lys
                            340             345             350
            Gln Ala Tyr Gly Glu Val Arg Glu Asp Gly His Pro Ile Val Phe Leu
                            355             360             365
            Ser Gly Gly Asp Ile Ser Arg Ile Leu Ile Lys Lys Gly Ile Asn Ser
                            370             375             380
            Thr Asp Ala Val Leu Ala Trp Leu Asn Ser Glu Phe Ser Lys Ser
            385                             390             395

<210> SEQ ID NO 2
<211> LENGTH: 159
<212> TYPE: PRT
<213> ORGANISM: Nitrolancea hollandica
```

<400> SEQUENCE: 2

| | | | | | | | | | | | | | | |
|---|---|---|---|---|---|---|---|---|---|---|---|---|---|---|
|Met|Asn|Leu|Glu|Asn|Leu|Thr|Thr|Arg|Glu|Leu|Leu|Ala|Val|Ser|Arg|
|1| | | |5| | | | |10| | | | |15|

Ala Ser Leu Arg Glu Leu Lys Arg Arg Gly Val Ile Arg Ser Gly Asn
            20                  25                  30

Ala Pro Ala Gly Asp Tyr Ala Glu Leu Leu Val Gln Arg Ala Thr Asp
        35                  40                  45

Gly Glu Leu Ala Asn Ala Ser Gln Lys Ser Trp Asp Ile Arg Thr Thr
    50                  55                  60

Glu Gly Asp Arg Leu Gln Val Lys Ala Arg Val Ile Thr Asp Glu His
65                  70                  75                  80

Ala Asn Gly Glu Arg Gln Leu Ser Thr Ile Arg Ser Trp Asp Phe Asp
                85                  90                  95

Ala Ala Val Ile Val Leu Phe Asp Asp Asn Phe Arg Val Trp Arg Ala
            100                 105                 110

Ala Arg Val Pro Ala Ala Ile Met Lys Glu Ala Ala Tyr Tyr Ser Gln
        115                 120                 125

His Val Arg Gly Tyr Thr Val Tyr Ala Lys Asp Ala Leu Leu Asn His
    130                 135                 140

Ser Glu Val Glu Asp Trp Thr Glu Gln Leu Arg Ser Val Glu Gln
145                 150                 155

<210> SEQ ID NO 3
<211> LENGTH: 168
<212> TYPE: PRT
<213> ORGANISM: Bacillus subtilis

<400> SEQUENCE: 3

Met Thr Val Ser Leu Lys Lys Leu Asp Asp Leu Glu Leu Thr Leu Leu
1               5                   10                  15

Tyr Ser Ser Leu Leu Lys Glu Leu Lys Gln Arg Gly Ile Ile Arg Thr
            20                  25                  30

Asn Asn Val Val Gly Glu Leu Gly Glu Tyr Leu Ala Ile Asn Phe Tyr
        35                  40                  45

Asn Lys Thr Lys Gly Leu Pro Lys Leu Gln Ala Ala Pro Thr Gly Thr
    50                  55                  60

Gln Asn Ile Asp Ala Leu Ser Ile Lys Gly Asp Arg Tyr Ser Ile Lys
65                  70                  75                  80

Thr Thr Thr Gly Ser Val Thr Gly Val Phe Tyr Gly Met Asn Asp Pro
                85                  90                  95

Glu Ile Arg Glu Pro Asp Ile Gln Lys Phe Glu Tyr Val Ile Ile Val
            100                 105                 110

Leu Phe Asp Lys Glu Tyr Ser Leu Lys Gly Ile Tyr Glu Leu Ser Trp
        115                 120                 125

Glu Ser Phe Ile Lys His Lys Arg Trp His Lys Arg Met Arg Ala Trp
    130                 135                 140

Asn Leu Thr Ile Thr Lys Ala Leu Leu Ser Asp Ser Glu Ile Ile Phe
145                 150                 155                 160

Glu Lys Glu Ser Lys Leu Leu Asn
                165

<210> SEQ ID NO 4
<211> LENGTH: 162
<212> TYPE: PRT
<213> ORGANISM: Pseudomonas amygdali -continued

```
<400> SEQUENCE: 4

Met Asn Met Glu Val Gln Asp Asp Val Tyr Glu Ile Leu Arg Glu Ala
1               5                   10                  15

Lys Ile Leu Ala Arg Arg Tyr Tyr His Leu Thr Gly Lys Pro Leu Gly
            20                  25                  30

Val Thr Gly Glu Val Ala Glu Tyr Glu Val Cys Arg Ile Leu Gly Leu
        35                  40                  45

Glu Leu Glu Gln Ala Arg Thr Ala Gly Phe Asp Ala Ile Glu Thr Arg
    50                  55                  60

Asp Gly Val Asp Leu Lys Val Gln Ile Lys Gly Arg Tyr Phe Pro Asn
65                  70                  75                  80

Ser Arg Met Arg Gly Gly Arg Leu Gly Ser Ile Asp Leu Lys Gln Pro
                85                  90                  95

Phe Asp Ile Val Met Leu Val Leu Leu Asp Gly Asp Tyr Asn Ala Phe
            100                 105                 110

Gln Ile Phe Glu Ala Gln Arg Pro Asp Val Glu Ala Ile Leu Thr Arg
            115                 120                 125

Pro Gly Ser Lys Ser Arg Asn Glu Arg Gly Ala Val Gly Ile Ser Gln
        130                 135                 140

Phe Lys Ala Ile Ser Ile Leu Arg Trp Glu Arg Glu Gly Val Asp Gln
145                 150                 155                 160

Pro Ala
```

ANALYSIS OF CHROMATIN USING A NICKING ENZYME

CROSS REFERENCE

This application is divisional application of U.S. application Ser. No. 16/327,698, filed Feb. 22, 2019, which is a § 371 application of International Application No. PCT/US2017/049556 filed Aug. 31, 2017, which claims the benefit of U.S. Provisional Application 62/383,151 filed on Sep. 2, 2016. The entire contents of these applications are incorporated herein by reference in their entirety.

BACKGROUND

The mammalian genome is largely packaged into chromatin consisting primarily of DNA, proteins and RNA. This macromolecular structure is further condensed into larger folded structures such as chromosomes during cell division. Cell cycle and the transcriptional status of the cell influence the state of the chromatin. It often undergoes remodeling events thus allowing switching between closed and open conformations, providing accessibility to DNA binding proteins including transcription factors (Zaret, et al. Curr Opin Genet Dev. 2016, 37:76-81; Weipoltshammer, et al. Histochem Cell Biol 2016, 145:343-358; Tsompana, et al., Epigenetics Chromatin 2014, 7:33). In addition to core histones, chromatin is composed of a wide variety of non-histone chromosomal proteins, which are involved in various activities, including DNA replication and gene expression (Radman-Livaja, et al., Dev Biol 2010, 339:258-26; Boyle, et al. Genome Res 2011, 21:456-464). A series of genome wide methods and studies for mapping chromatin accessibility (open chromatin), nucleosome positioning and transcription factor occupancy have been established to decipher the epigenetic information encoded in chromatin (Schones, et al. Cell 2008, 132:887-898; Shivaswamy, et al. PLoS Biol 2008, 6:e65; Lee, et al. Nat Genet 2004, 36:900-905; Boeger, et al. Mol Cell 2003, 11:1587-1598; Wallrath et al. Bioessays 1994, 16:165-170; Hogan, et al. PLoS Genet 2006, 2:e158; Korber, et al. Mol Cell Biol 2004, 24:10965-10974; Shu, et al. Nucleic Acids Res 2011, 39:7428-7443; Buck, et al. Nat Genet 2006, 38:1446-1451).

Early studies identified nucleosome depleted regions as being hypersensitive to DNase I, and those regions lack proteins and are associated with gene activation in eukaryotic organisms (Wu, et al. Cell 1979, 16:807-814; Wu, Nature 1980, 286:854-860; Keene, et al. Cell 1981, 27:57-64; Levy, et al. Nature 1981, 289:198-203). Although all these methods are powerful on their own, they all require specific reagents and relatively large amounts of cells. For example, mapping of open chromatin by DNase-seq requires between one million to ten million cells and often involves titration of enzyme and multiple steps before the library is made for sequencing. Similarly, transcription factor binding sites can be interrogated using chromatin-immunoprecipitation (ChIP) sequencing technology (Park, Nat Rev Genet 2009, 10:669-680). The major drawback of this method is the availability and specificity of appropriate antibodies. Recently, DNase I hypersensitive site mapping has been performed with an improved protocol by adding circular carrier DNA, referred to as single cell DNase I seq (scD-NaseI-seq). This technology employs between 1 and 1,000 cells. In single cells, highly expressed genic regions with multiple active histone marks displayed constitutive DNase I hypersensitive sites. However coverage was limited with the mappability of 1000 cells to the reference genome at 40% and single cells at 2% (Jin, et al., Nature 2015, 528:142-146).

There are three commonly used methods for open chromatin and regulatory site identification by sequencing. These are: DNase-seq (DNase I hypersensitivity site sequencing), FAIRE-seq (Formaldehyde Assisted Isolation of Regulatory Element sequencing; FAIRE) and Assay for Transposase-Accessible Chromatin using sequencing (ATAC-seq (Nagy, et al. Proc Natl Acad Sci USA 2003, 100:6364-6369; Crawford, et al. Genome Res 2006, 16:123-131; Buenrostro, et al. Nat Methods 2013, 10:1213-1218). DNase-seq relies on the preferential digestion of nucleosome and transcription factor depleted regions of chromatin using DNase I followed by sequencing of the digested DNA. FAIRE-seq enriches the nucleosome depleted DNA using formaldehyde fixation, sonication and phenol/chloroform extraction of the non protein-bound DNA followed by sequencing. ATAC-seq uses a hyperactive Tn5 transposes to integrate its adaptor payload preferentially into accessible open chromatin regions. A problem with this approach is the generation of non-specific adapter integration and amplification of non-nuclear DNA such as mitochondrial genome. The mitochondrial genome is represented in up to half of all reads. Both DNase-seq and FAIRE-seq can be implemented on fixed cells, whereas ATAC-seq works on unfixed cell nuclei. Furthermore, there is no common protocol for chromatin occupancy mapping in both unfixed and fixed cells.

There is an unmet need for a fast, accurate, and robust method for analyzing open chromatin in fixed and unfixed cells both at the DNA sequence level for molecular diagnostics and at the level of the intact nuclei for histological analysis. There is also a need to develop molecular analysis/diagnostic methods for the detection of chromatin signatures in both fixed and unfixed cells as an indicator of cancerous and non-cancerous tissues in a biopsy. A fast reliable enzymatic technique for detecting genome instability and an altered chromatin state would be beneficial for cancer patients and the medical community treating suspected carcinomas

SUMMARY

Provided herein are compositions and methods for analyzing open and/or closed chromatin using a nicking enzyme. Where detection and/or sequencing of open chromatin (euchromatin) is desired, the nicking enzyme may nick the DNA after recognizing a sequence that contains only unmethylated cytosine or contains a mixture of methylated and unmethylated cytosines. An example is Nt.CviPII (New England Biolabs, Ipswich, MA) that nicks DNA at CCD sequence or at C$^m$CD, but not at $^m$C$^m$CD. Examples of other nicking enzymes are described herein that target open chromatin. Where detection and/or sequencing of closed chromatin (heterochromatin) is desired, the nicking enzyme may nick the DNA at recognition sequences that contain methylated cytosine (for example, $^m$CpG) and does not nick unmethylated sequences. In subsequent descriptions of methods used to analyze chromatin, examples may be provided in which open chromatin only is specified. However, the same methods are applicable to closed chromatin depending on the nicking enzyme that is selected according to the above.

In some embodiments the method may be used to detect open and/or closed chromatin in fixed or unfixed cell nuclei. The method may use enzymes that are methylation dependent, methylation independent and/or methylation sensitive, thereby allowing the analysis of methylated sequences or unmethylated sequences including enrichment or visualization. In these embodiments, the method may comprise obtaining a sample containing permeabilized cell nuclei, wherein the cell nuclei comprise chromatin; reacting the cell nuclei with a composition comprising a nicking enzyme, four dNTPs, at least one labeled dNTP such as two or more labeled dNTPs, and a polymerase, to selectively label the chromatin; and analyzing the labeled nuclei, wherein the analyzing is done by: detecting an optically-detectable signal from the cell nuclei, if the at least one labeled dNTP comprises an optically detectable label; or enriching for and then sequencing labeled DNA fragments that comprise the labeled nucleotide, if the labeled nucleotide comprises an affinity tag.

In some embodiments, the method comprises obtaining a sample comprising chromatin (e.g., isolated chromatin, isolated permeabilized nuclei, or permeabilized cells, which may be fixed or unfixed) and reacting the sample with a nicking enzyme, a polymerase, four dNTPs and at least one or more labeled dNTPs (or two or more labeled dNTPs) to selectively label the chromatin in the sample. In some embodiments, the nicking enzyme produces nicks in accessible regions of the DNA in the sample (i.e., in the open chromatin), and the polymerase adds the at least one (or two or more) labeled nucleotides to the nick sites (e.g., to the 3' hydroxyl at those sites). In other embodiments, the nicking enzyme may only recognize methylated sites, e.g., methylated CpGs, in which case only sequences adjacent or approximate to the methylated nucleotides will be nicked and labeled. Addition of the labeled nucleotide(s) facilitates analysis of the chromatin. For example, if the labeled nucleotide(s) comprises an optically detectable label, then the labeled sample may be analyzed by detecting an optically-detectable signal. In this embodiment, the analysis may be performed by microscopy (e.g., fluorescence microscopy) to produce an image of at least part of the sample. In another example, if the labeled nucleotide(s) comprises an affinity tag, then the labeled sample may be analyzed by enriching for fragments that comprise the labeled nucleotide(s). The enriched fragments may be sequenced and optionally mapped to a referenced genome. In these embodiments, the sequence reads should correspond to open chromatin. The sequence reads can be used to determine whether a particular sequence is in open or closed chromatin, or to make a chromatin accessibility map.

Embodiments of the methods described herein may have certain advantages over methods used in the prior art. For example, the amount of nicking enzyme does not need to be titrated prior to use. Further, as will be shown below, embodiments directed to labeling open chromatin may be employed to rapidly identify cells with altered characteristics of growth and division such as cancerous cells in a tissue section. Specifically, cells may be rapidly "stained" using present embodiments either directly using, for example, a dye modified nucleotide, or indirectly, using, for example, a secondary reagent that reacts with a modified nucleotide such as an antibody or stain. Embodiments of the method provide a means to identify cells that have altered chromatin within a few minutes rather than hours or days. For example, the plasma membranes, cell wall and nuclei in a fixed or unfixed tissue section may be permeabilized and then treated with a nicking enzyme, a polymerase and a nucleotide comprising an optically detectable label, thereby selectively adding the optically detectable label to the open chromatin in the cells. Because cancerous cells often have more genome instability and open chromatin than neighboring non-cancerous cells, the cancerous cells in a tissue section can be potentially identified immediately. Finally, reliable results can be obtained from a relatively low number of cells (e.g., as low as 25, 50, 100, or 250 cells).

The random nicking activity of DNase I (which is not considered a nicking enzyme herein) can be compared with a sequence-specific nicking enzyme such as Nt.CviPII and its impact on open chromatin identification. Nt.CviPII recognizes the CCD trinucleotide sequence and these sites are densely dispersed throughout the human genome. Moreover, the open chromatin is readily accessible by the nicking enzyme. Importantly, while DNase I sequencing bookmarks the ends of the open chromatin, the nicking enzyme based methods described herein actually capture the open chromatin sites between nucleosomes.

In some embodiments, a composition comprising: a nicking enzyme, a polymerase, four dNTPs and a labeled dNTP is provided. In some embodiments, the composition may further comprise chromatin. In these embodiments, the chromatin may comprise open chromatin and closed chromatin, and at least some of the open chromatin may be labeled by the labeled nucleotide. In some embodiments, the composition may comprise an isolated nucleus, and the chromatin is contained within an isolated nucleus. In other embodiments, the composition may comprise a permeabilized cell, wherein the chromatin is contained in the permeabilized cell. In some embodiments, the cell may be a fixed cell. In other embodiments, the cell may be an unfixed cell. In some embodiments, the composition may comprise a clinical sample, e.g., a tumor biopsy. In some embodiments, the labeled nucleotide may comprise a detectable label, e.g., a fluorophore. In other embodiments, the labeled nucleotide may comprise an affinity tag such as a biotin moiety. In those embodiments that in which the chromatin is within the nucleus of cells in a biopsy cell sample or clinical sample for microscope examination, the composition may comprise: an enzyme selected from a nicking enzyme and DNase I. In one embodiment of the composition, the nicking enzyme is methylation-dependent. For example, the nicking enzyme may nick at methylated CpGs. In an alternative embodiment of the composition, the nicking enzyme is methylation-sensitive. Methylation-dependent and methylation-sensitive nicking enzymes are known in the art, and examples are provided herein.

In some embodiments, the method may comprise: (a) obtaining a sample comprising chromatin; (b) reacting the sample with a nicking enzyme, a polymerase and a labeled nucleotide to selectively label the open chromatin in the sample; and (c) analyzing the labeled sample of (b). In some embodiments, the analyzing is done by: (i) detecting an optically-detectable signal from the sample, if the labeled nucleotide comprises an optically detectable label; and/or (ii) enriching for and then sequencing fragments that comprise the labeled nucleotide, if the labeled nucleotide comprises an affinity tag. In some embodiments, the labeled nucleotide comprises an optically detectable label and the analyzing step of (c) is done by microscopy to produce an image of at least part of the sample. In other embodiments, the labeled nucleotide may comprise an affinity tag and the analyzing step of (c) includes: i. fragmenting the DNA in the sample, ii. enriching for fragments that contain the labeled nucleotide and iii. sequencing the enriched fragments. In one embodiment of the method, the nicking enzyme is methylation-dependent. For example, the nicking enzyme may nick at methylated CpNs including $^{5m}$CpG. In an alternative embodiment of the method, the nicking enzyme is methylation-sensitive. Methylation-dependent and methylation-sensitive nicking enzymes are known in the art, and examples are provided herein.

As noted above, in some embodiments, the sample may comprise an isolated nucleus, and the chromatin is contained within an isolated nucleus. In other embodiments, the sample may comprise a permeabilized cell, and the chromatin is contained in the permeabilized cell. In some embodiments, the cell is a fixed cell. In other embodiments, the cell is an unfixed cell. In some embodiments, the composition may comprise a clinical sample, where the cell is in the clinical sample. The clinical sample is a tumor biopsy.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way. Although some of the drawings illustrate the use of the combination of biotin-dATP/dCTP, this is not intended to be limiting. Any one or more (e.g. two or more) labeled dNTPs can be used in the methods and compositions of the invention.

FIG. 1A shows a cartoon depicting closed chromatin (heterochromatin) in which DNA is coiled tightly around nucleosomes.

FIG. 1B shows a cartoon where the chromatin is open (euchromatin) (see Gaspar-Maia, et al. Nat Rev Mol Cell Biol. 2011 12:36-47).

FIG. 1C is a cartoon depicting (i) nicking of genomic DNA at open chromatin sites (here exemplified with the nickase Nt.CviPII) (ii) repairing the nick with a DNA polymerase and all four nucleoside triphosphates (dNTPs) plus 2 modified NTPs e.g. biotin-dATP and biotin-dCTP) (Biotin-dATP/dCTP) that permit labeling of the open chromatin. Big circles correspond to nucleosomes, small circles correspond to labeled dNTP.

FIG. 2A shows a flask of cultured cells (1) that may be either fixed in a preservative, e.g., formaldehyde or remain unfixed (2) so that the nuclei are either fixed or unfixed (3). The nuclei are then labeled using a nicking enzyme (e.g., Nt. CviPII), a polymerase, 4dNTPs and modified dNTPs (e.g., Biotin-dATP/dCTP) (4).

FIG. 2B shows a series of DNA dot blots. In these experiments, two fold dilutions of denatured genomic DNA (starting at 4 µg) from unfixed (5) and formaldehyde-fixed nuclei (6) and labeled using a combination of nicking enzyme (Nt.CviPII), DNA polI, 4dNTPs and modified dNTPs (Biotin-dATP/dCTP), were blotted on the membrane. The amount of labeling was detected using an HRP-conjugated goat anti-biotin antibody. None of the DNA is labeled in the absence of DNA polymerase I (New England Biolabs, Ipswich, MA).

Figure 1A:
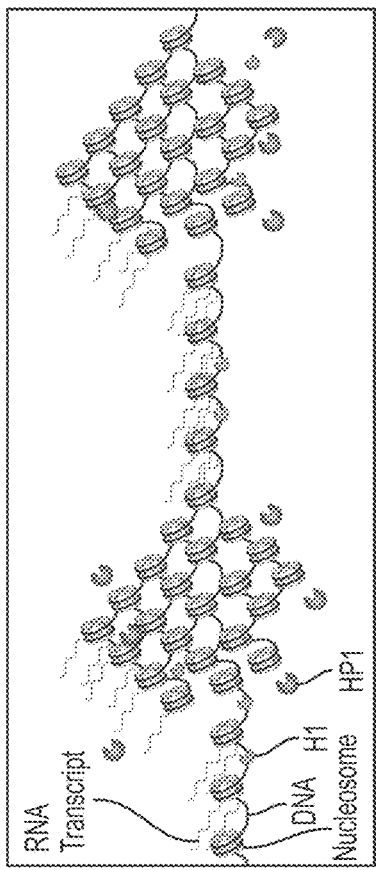
FIG. 1A-1C provides a schematic of an embodiment of the method for labeling open chromatin.

The chromatin crosslinking was reversed and genomic DNA isolated (7). The isolated genomic DNA was fragmented (8) and a standard library prepared, including for example, end-repair dA tailing and adapter ligation (9). The labeled genomic DNA fragments were then enriched by for example, capturing biotinylated labeled genomic DNA fragments with streptavidin beads (10). The enriched DNA was amplified optionally using barcoded primers (11) and the fragments analyzed on a bioanalyzer and/or sequencing the enriched genomic fragments (12).

FIG. 4A-4D shows that nicking enzyme recognition sequences that occur in closed chromatin are not cleaved, labeled and enriched using the present method, in contrast to open chromatin. This data shows that the present method is relatively unbiased.

Figure 4A:
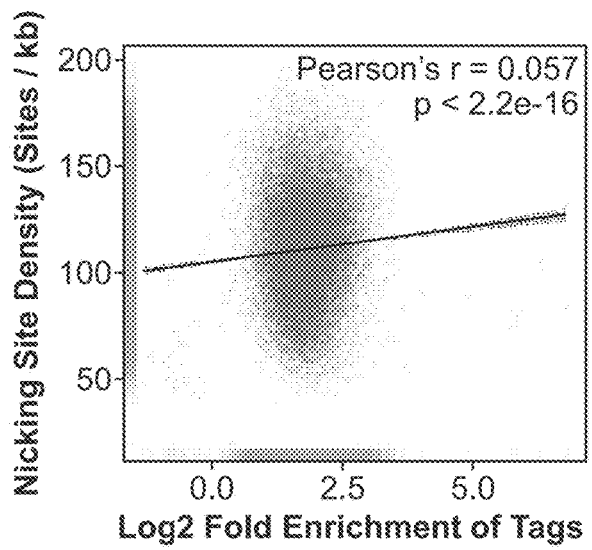

FIG. 4A shows a plot of nicking site density (y-axis) against Log 2 fold enrichment of tags (x-axis). Pearson's correlation test gave an r of 0.057 and $p<2.2\ E^{-16}$ showing no correlation between nicking site density and log 2 fold enrichment of sequencing tags.

Figure 4B:
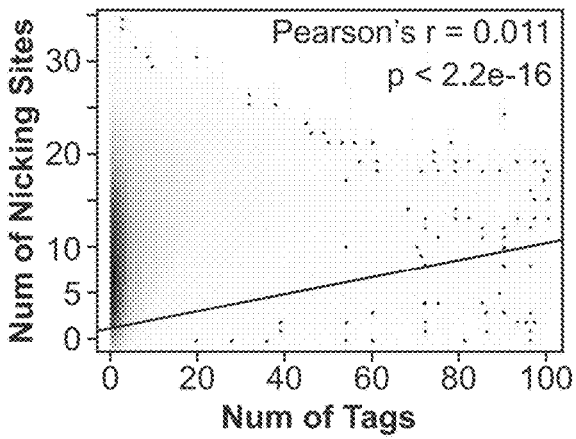

FIG. 4B shows a scatter plot corresponding to the number of tags on the x-axis and the number of nicking sites on the y-axis. Pearson's correlation test gave an r of 0.011 and $p<2.2\ E^{-16}$ showing no correlation between number of nicking sites and number of sequencing tags.

Figure 4C:
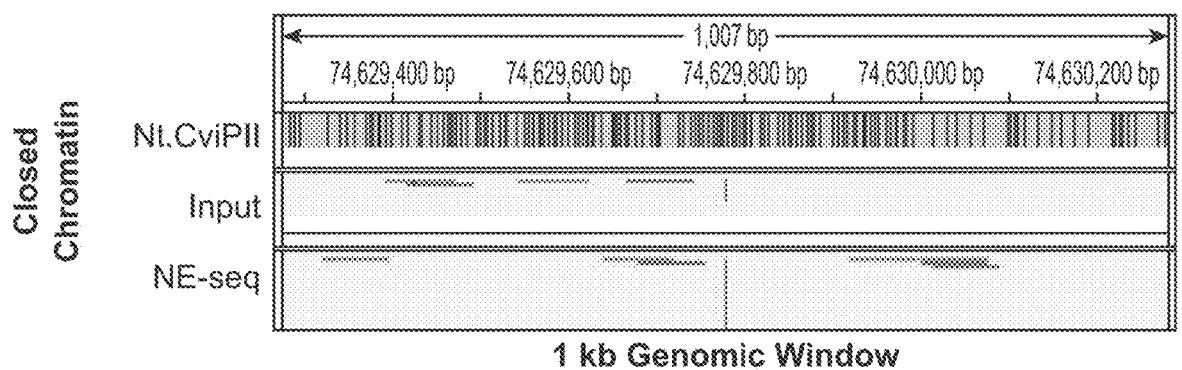

FIG. 4C shows the profile for closed chromatin from HCT116 in a 1 kb window of the human genome (hg19). The section labeled Nt.CviPII shows the distribution of CCD recognition site distribution in human genome. The section labeled Input shows the unenriched sequencing reads. The section labeled NE-seq which enriches for open chromatin shows lack of enrichment of sequencing reads in closed chromatin.

Figure 4D:
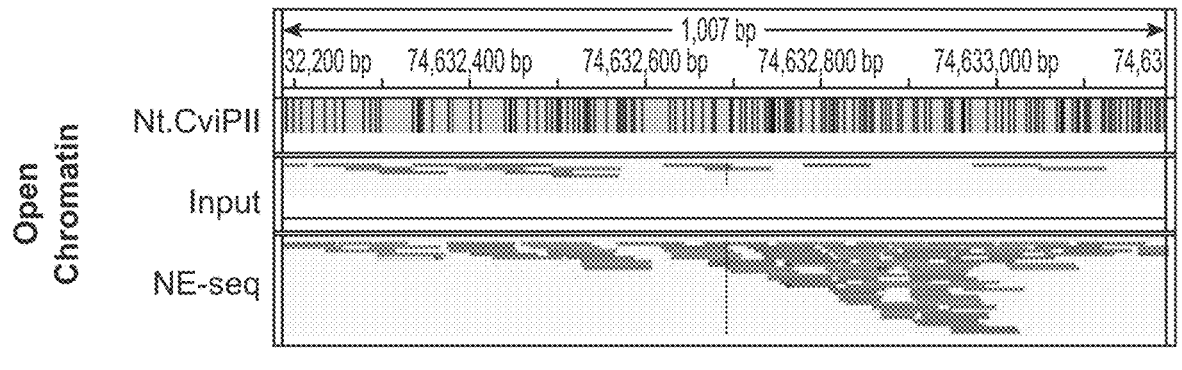

FIG. 4D shows the profile for open chromatin from HCT116 in a 1 kb window of the human genome (hg19). The section labeled Nt.CviPII shows the distribution of CCD recognition site distribution in human genome. The section labeled Input shows the lack of enrichment of sequencing reads. The section labeled NE-seq shows strong enrichment of sequencing reads, in open chromatin.

FIG. 5A-5C shows that embodiments of the method can provide reliable open chromatin profiling from as few as 25 cells.

FIG. 5A shows the degree of overlap in the number of reads in a Venn diagram between the open chromatin sites (OCS) identified from 250, 2,500, 25,000, and 250,000 cells. 47102 OCS are common to all 4 samples containing different numbers of cells.

FIG. 5B shows a screenshot of the Integrative genomics viewer (IGV) browser (Integrative Genomics Viewer, Nature Biotechnology 2011 29, 24-26) showing the alignment of identified OCSs from 25 to 250,000 cells in a window of 39 kb. Profiling of varying numbers of cells involving library construction (here 25-250,000 cells) with the same standard protocol except for 25 and 250 cells. In the case of 25 cells, 0.25 U of Nt.CviPII and 5 U of DNA polymerase I were added. For both 25 and 250 cells, 10 µg of glycogen was added during genomic DNA extraction and entire labeled genomic DNA was sonicated and used for library generation. Finally, 10 μL of streptavidin beads were added to capture the biotinylated DNA, which was used as template for library amplification.

FIG. 5C shows a screenshot of the IGV browser showing the alignment of identified OCSs from 25 to 250,000 cells in a window of 10 kb as described in FIG. 5B.

Figure 6:
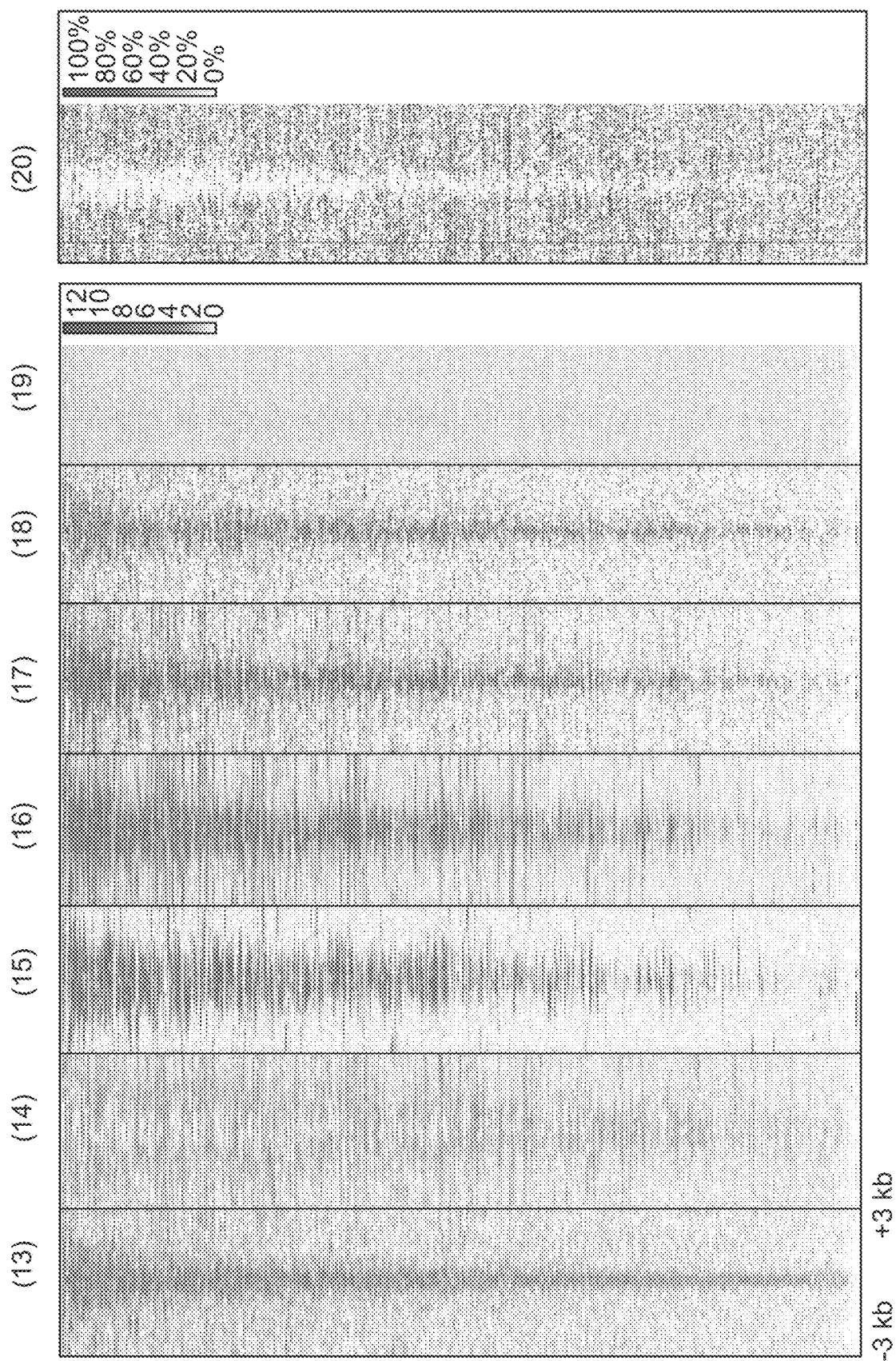

FIG. 6 shows a heat map obtained from the genome sequence of HCT116 (colorectal cancer cell line) around an open chromatin locus (with a 3 kb upstream and downstream window respectively) correlated with histone marks, transcription factor and RNA pol II (ChIP seq data from ENCODE).

(19) is a heat map of labeled "input" provides background signal obtained using whole genome sequence.

(13) is a heat map of labeled OCS. NE-seq shows enriched OCS where the increased signal in the center of the heatmap corresponds to the presence of a higher concentration of sequence tags compared to other regions in the plot;

(20) is a heat map in which depletion of CpG methylation is observed at OCS peaks. Methylation of cytosine residues present in a window of +/−3 kb around the OCS were plotted using a scale of 0 (white) to 1 (colored), with 0 representing no methylation and 1 representing 100% methylation;

(14) is a heat map for labeled H3K4me1 showing enrichment of enhancer elements as seen with the increased signal in the center of the heatmap correlating with the presence of higher sequence tags as opposed to other regions in the plot;

(15)-(18) are heat maps for labeled H3K4me3, H3K27ac, RNA pol II and YY1 respectively, where all show enrichment of corresponding histone marks, RNA pol II occupancy and transcription factors at open chromatin. H3K4me3, H3K27ac are histone marks associated with open chromatin while H3K4me1 is a histone mark associated with enhancer regions. Regions having RNA pol II or transcription factor (YY1) binding are actively transcribed and are associated with open chromatin. The signal from the sequencing tags for each experiment was plotted using a scale of 0 (white) to 12 (colored). The darker color in the center of the lanes for each dataset corresponds to an enriched signal for OCS NE-seq.

FIG. 7A-7E shows that NE-seq is sensitive and generates similar results for fixed and unfixed (not fixed) cells and various cell types. The method was carried out according to FIG. 3.

FIG. 7A shows a Venn diagram with an overlap between the OCSs obtained using NE-seq for fixed cells and unfixed HCT-116 cells.

FIG. 7B is a display of open chromatin peaks for fixed and unfixed cells obtained from NE-seq in a screenshot of the IGV browser. The peaks are highlighted.

FIG. 7C shows a Venn diagram for OCSs in HCT116 (colorectal tumor cells) and MCF7 (breast tumor cells) determined by NE-seq. The common and unique OCSs are shown.

FIG. 7D displays results of open chromatin peaks for HCT116 and MCF7 obtained from NE-Seq in a screenshot of the IGV browser. The peaks are highlighted.

FIG. 7E shows the differential distribution of OCS for the two cell types (HCT116 and MCF7) in multiple annotated genomic regions (5' untranslated region (UTR), promoter, intergenic region, intron, exon, transcriptional start site (TTS) and 3'UTR).

Figure 8A:
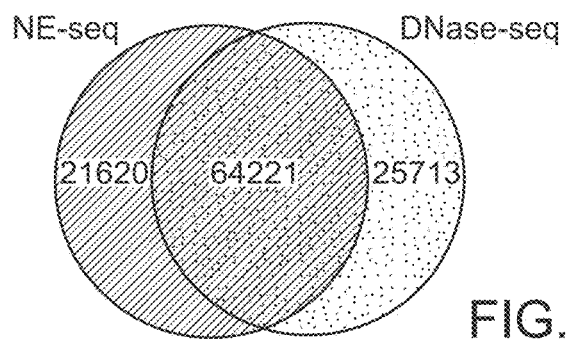
Figure 8B:
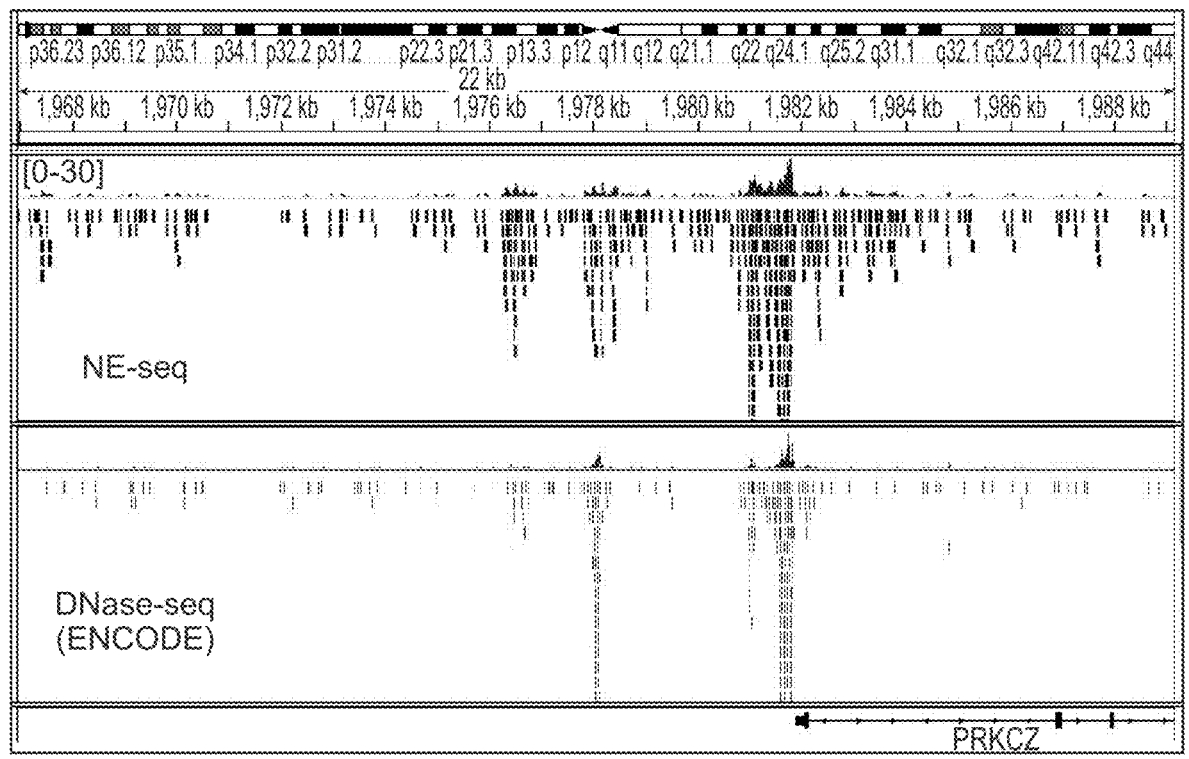
Figure 8C:
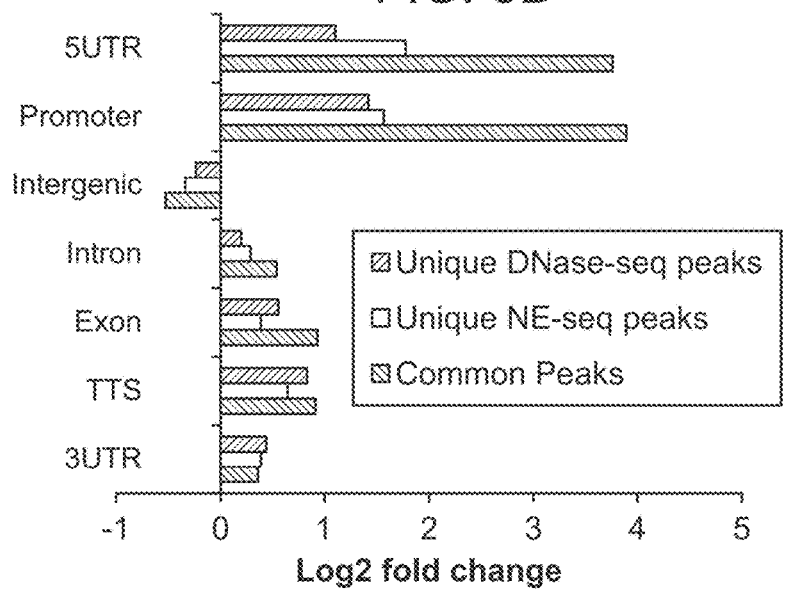

FIG. 8A-8C provides a comparison between the peak distribution of an embodiment of the present method using NE-seq (see the Example) and the prior art method that utilized DNAse I (DNase-seq).

FIG. 8A shows a Venn diagram with an overlap of 64221 open chromatin regions/peaks between the OCS and DHS identified by NE-seq and DNase-seq for fixed HCT-116 cells.

FIG. 8B shows the results of sequencing fragments that had been enriched using NE-seq in the top panel while the bottom panel shows results with DNase-Seq obtained from ENCODE.

FIG. 8C shows a comparison of the distribution of DNase-seq peaks and NE-seq peaks for the identified annotated genomic regions-5'untranslated region (UTR), Promoter, Intergenic regions, introns, exons, transcriptional termination sites (TTS), 3'UTR. Unique DNase-seq peaks, unique NE-seq peaks, and common peak distribution are shown.

Figure 9:
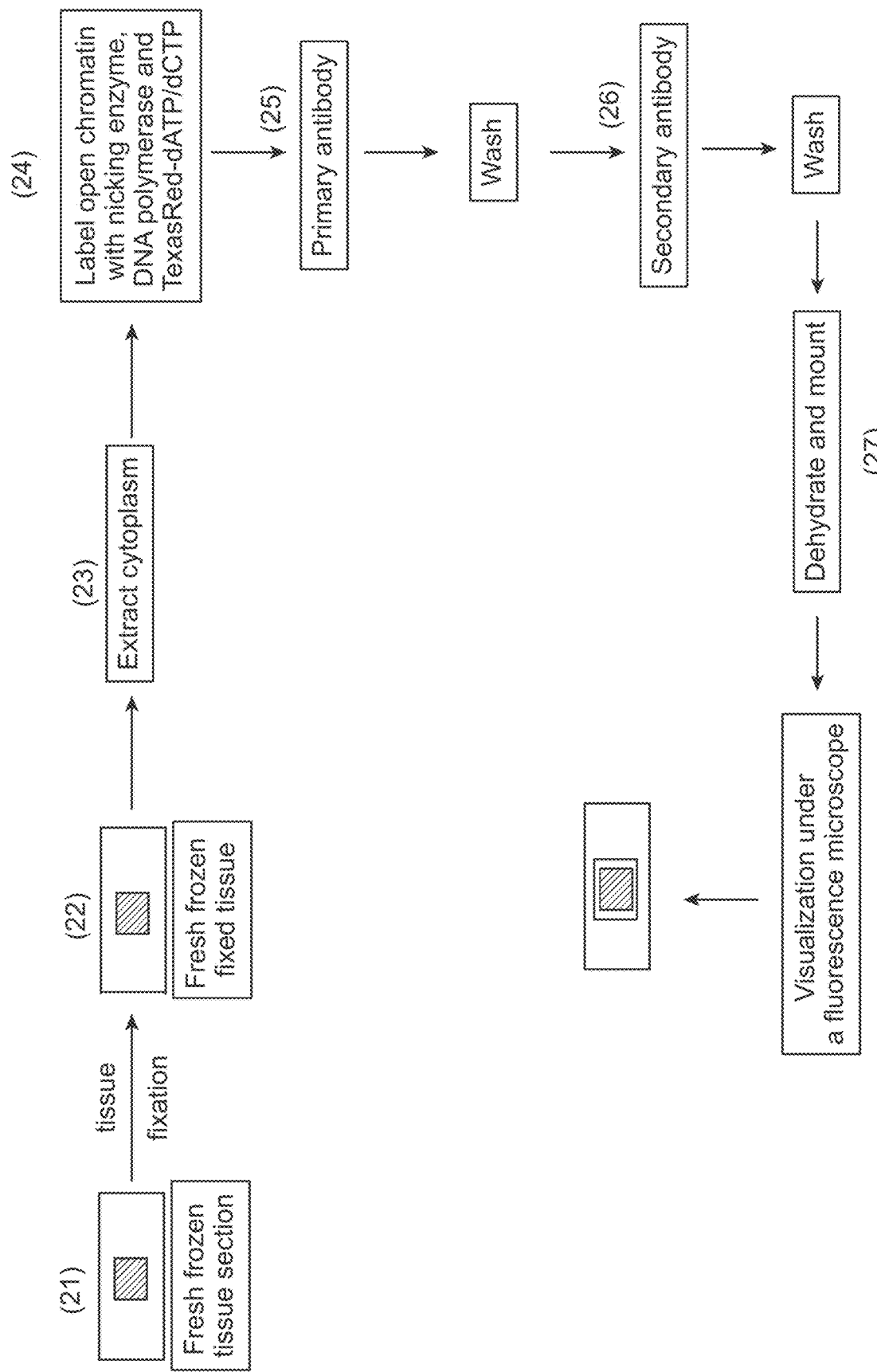

FIG. 9 is a flow diagram of an embodiment of the method for visualizing cancer and non-cancer cells and differentiating them in biopsy samples. This flow diagram describes obtaining a fresh frozen tissue section (21); fixing the tissue (22); extracting cellular cytoplasm (23); labeling chromatin using nicking enzyme and DNA polymerase with Texas® Red-5-dATP and Texas Red®-5-dCTP (PerkinElmer, Waltham, MA) (24); staining with a primary antibody (for example Herceptin for identifying breast cancer cells) (25); washing and staining with a fluorescently labeled secondary antibody (26); dehydrate and mount the slides for visualization (27). The slides were visualized by fluorescent microscopy optionally obtaining a density plot of open chromatin in the nucleus of cells (28).

Figures 10A, 10B:
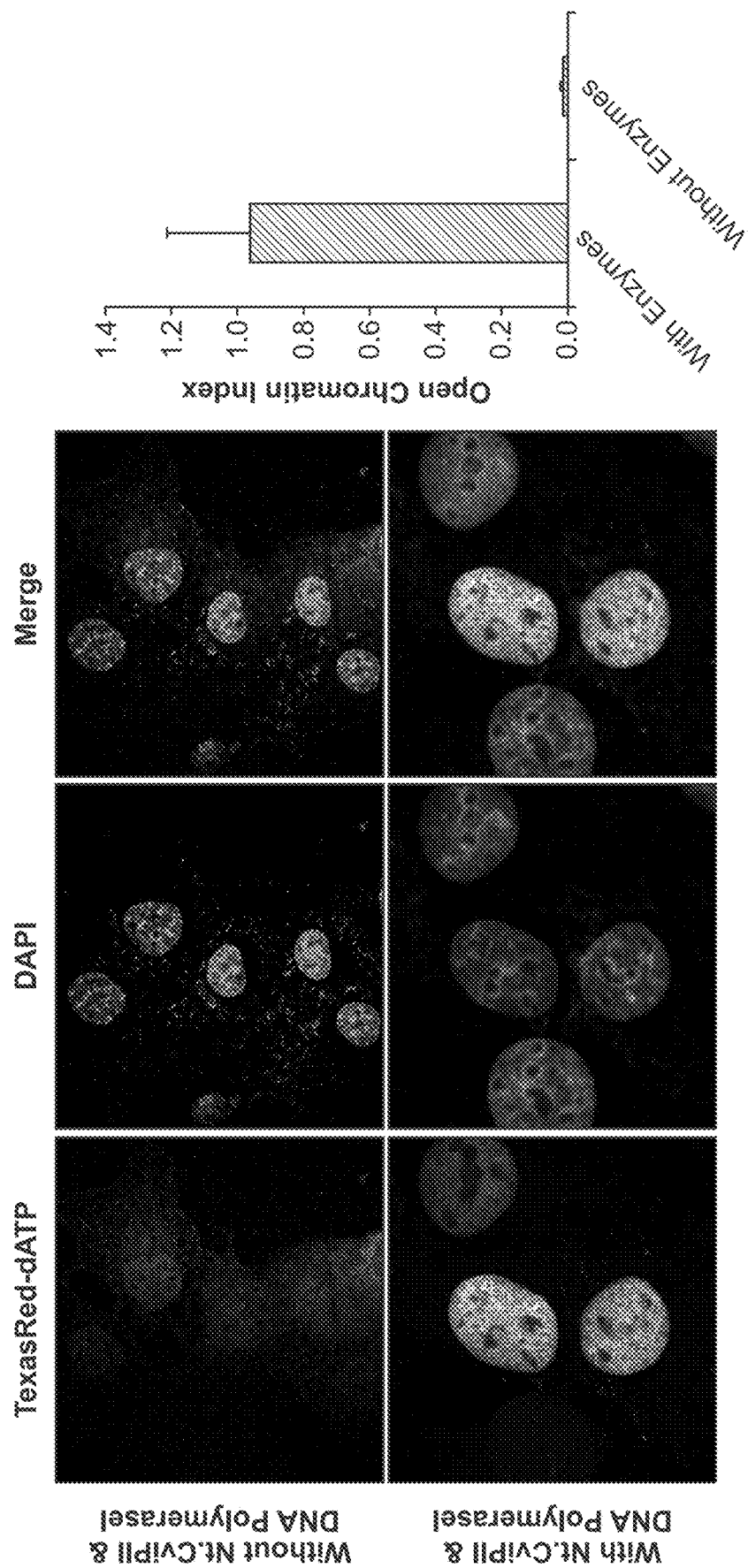

FIG. 10A-10B shows open chromatin labeling in fixed HeLa cells using a nicking enzyme, polymerase and all four dNTPs (dATP, dCTP, dGTP, dTTP) supplemented with Texas Red-5-dATP.

FIG. 10A: Texas Red-5-dATP was added to the cells in both top and bottom panels. Non-specific nuclear staining was performed using DAPI and/or the OCS specific Texas Red-5-dATP staining. The column headed "Merge" represents the co-localization of the open chromatin in the nucleus (visualized as a magenta stain, resulting from both the DAPI staining (blue) and Texas Red-5-dATP staining (Red)). The three images horizontally placed in the first row show the results of labeling reaction performed in the absence of Nt.CviPII and DNA polymerase I. The three images horizontally placed in the second row show labeling reaction performed in the presence of Nt.CviPII and DNA polymerase I.

FIG. 10B shows a bar graph in which the labeling of OCSs occurs only in the presence of nicking enzyme mix (Nt.CviPII and DNA polymerase I) and not in the absence of enzymes. Y-axis represents the ratio of the mean intensity of the red pixels to the mean intensity of the blue pixels (Open Chromatin Index (OCI)).

Figure 11B:
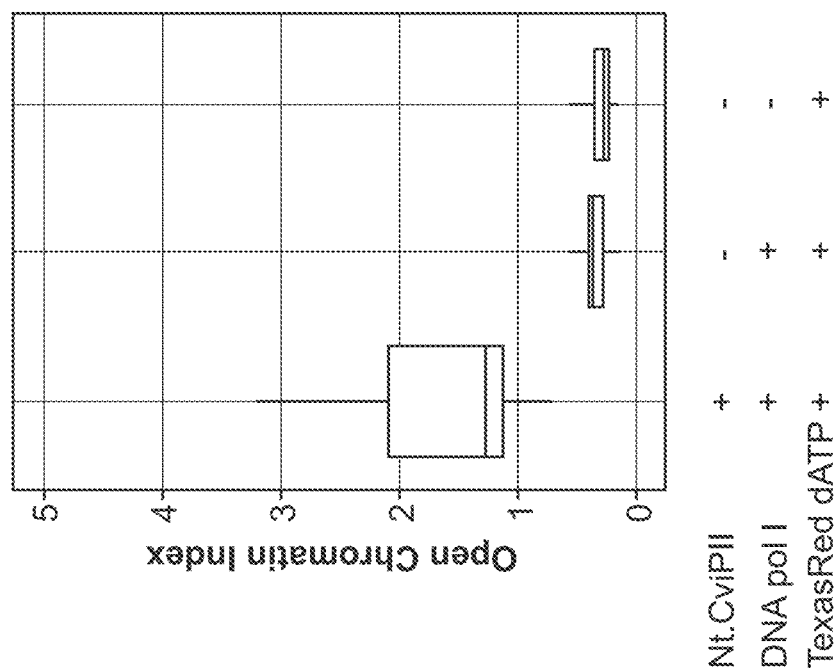
Figure 11A:
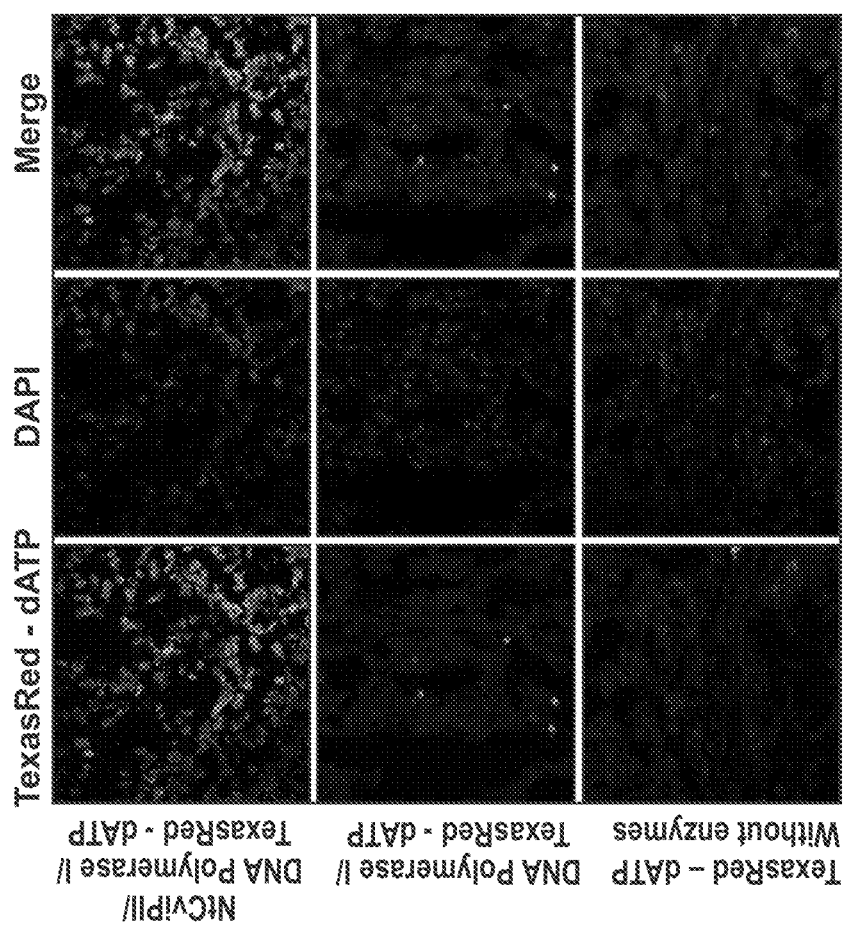

FIG. 11A-11B shows open chromatin labeling in fresh frozen acetone fixed breast cancer tissue sections. Texas Red-5-dATP, a fluorescent dye that can be used in nick translation, or 4,6-Diamidino-2-phenylindole (DAPI) (Thermo Fisher Scientific, Waltham, MA), was added to the cells. DAPI is a blue fluorescent DNA stain that exhibits 20 fold enhancement of fluorescence upon binding to AT regions of ds DNA.

FIG. 11A: the top row of pictures shows the results of labeling of fixed cells in the presence of Nt.CviPII and DNA polymerase I. The middle row of pictures shows the results of labeling with DNA polymerase I in the absence of Nt.CviPII. The third row of pictures shows the results of labeling in the absence of Nt.CviPII and DNA polymerase I. The first column of pictures shows the results using Texas Red-5-dATP, the second column shows the results of DAPI staining, and the third column shows the merged images from stained cells.

FIG. 11B shows the boxplot depicting the labeling efficiency of OCSs. Y-axis represents the ratio between the mean intensity of the red pixels to the mean intensity of the blue pixels (OCI).

Figure 12:
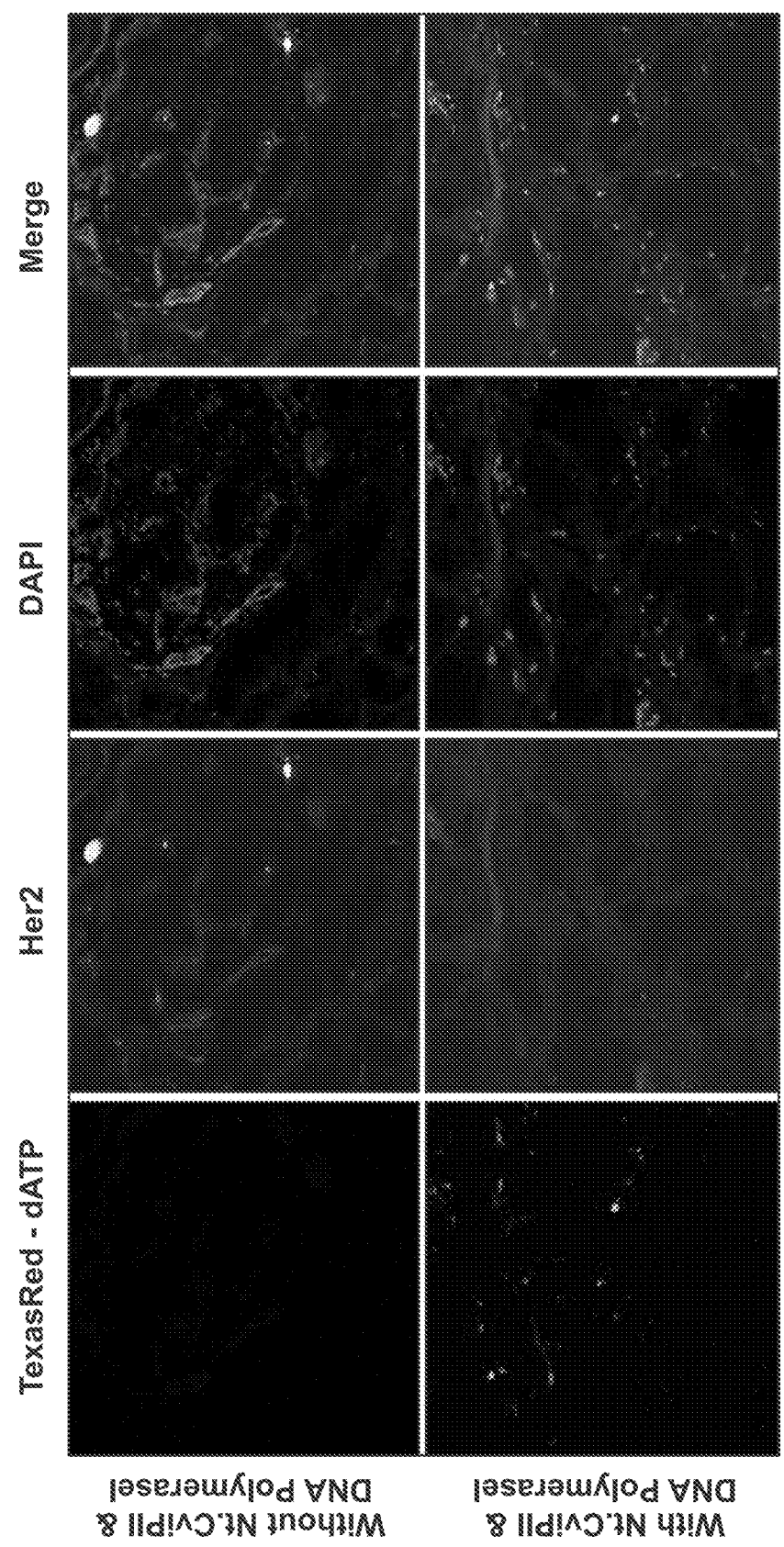

FIG. 12 shows exemplary results from open chromatin labeling of a fresh frozen acetone fixed Her2+ normal adjacent breast tissue section using Texas Red-5-dATP (column 1), anti-her-2 antibody (column 2) DAPI (column 3) or merged images of column 1, column 2, and column 3 (column 4).

The top row of images show results of a labeling reaction performed in the absence of Nt.CviPII and DNA polymerase I.

The bottom row of images show results of a labeling reaction performed in the presence of Nt.CviPII and DNA polymerase I.

Figure 13:
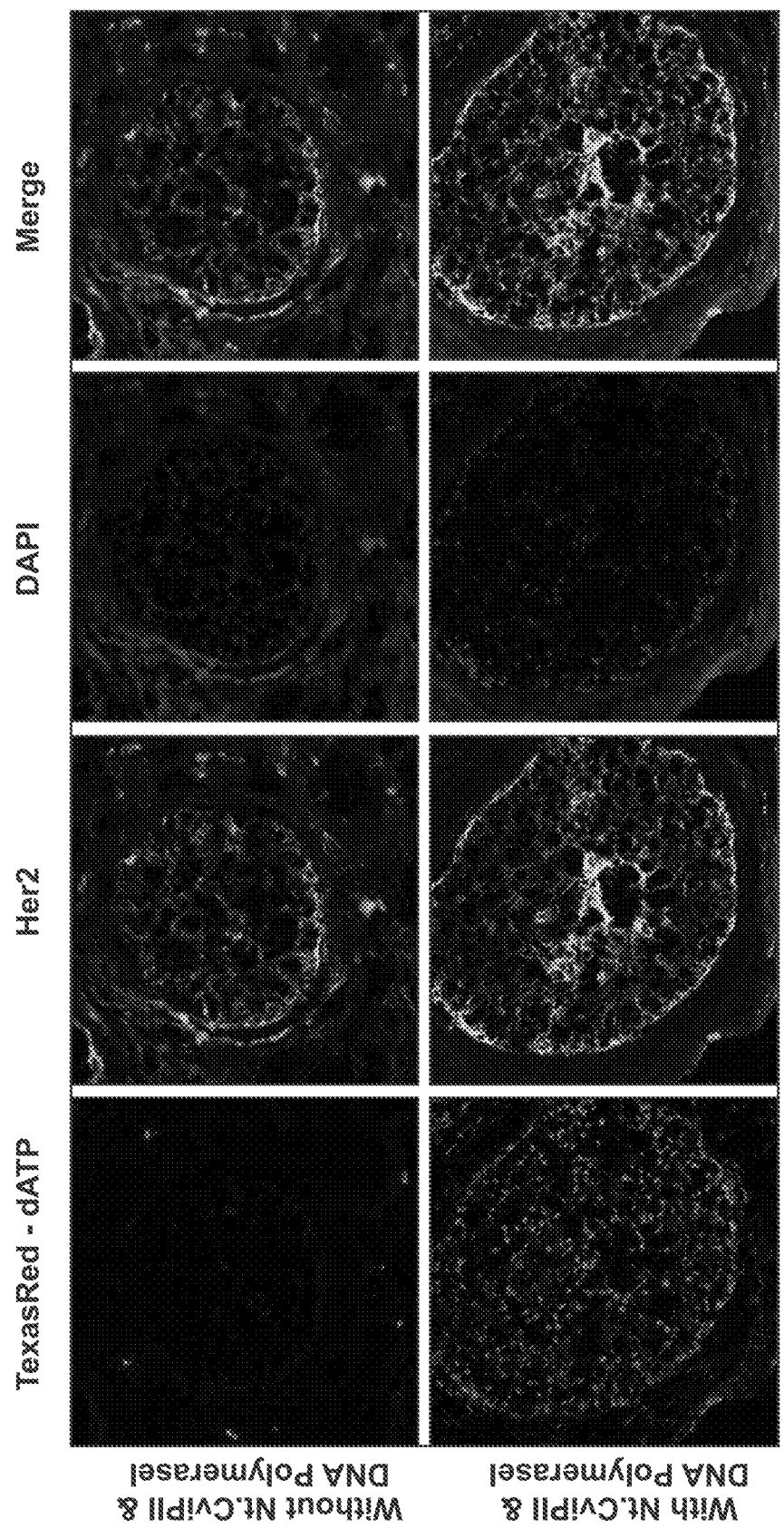

FIG. 13 shows exemplary results from open chromatin of a fresh frozen acetone fixed Her2 positive breast cancer tissue section using Texas Red-5-dATP (column 1), anti-her-2 antibody (column 2), DAPI (column 3) or merged images of column 1, column 2, and column 3 (column 4) The top row of images show results of a labeling reaction performed in the absence of Nt.CviPII and DNA polymerase I.

The bottom row of images show results of a labeling reaction performed in the presence of Nt.CviPII and DNA polymerase I. Both tissue sections examined in FIG. 12 and FIG. 13 are from the same patient.

Figure 14:
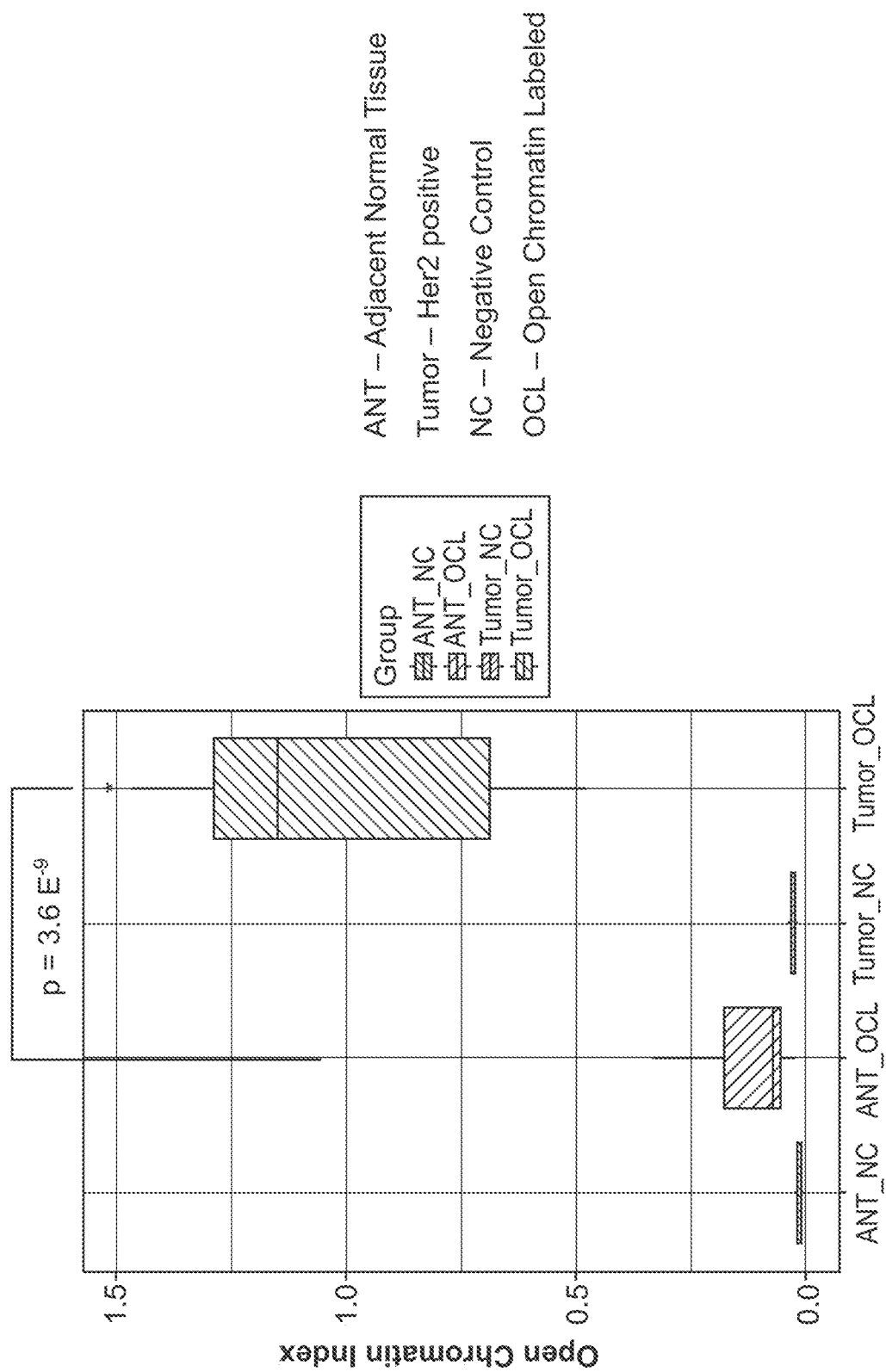

FIG. 14 shows a boxplot illustrating the labeling efficiency of open chromatin sites in tumor cells and adjacent normal cells from FIG. 12 and FIG. 13. In this figure, the y-axis represents the ratio of the mean intensity of the red pixels to the mean intensity of the blue pixels (OCI). ANT—Adjacent Normal Tissue; Tumor—Her2 positive; NC—Negative Control; OCL—Open Chromatin Labeled.

FIGS. 15A and 15B shows images of the first and last step of NE-seq to label and analyze open chromatin I in cancer tissue sections. This embodiment uses the first 4 steps shown in FIG. 9, namely (21)-(23) followed by steps (4) and (7)-(12) in FIG. 3.

FIG. 15A shows an image of a fresh frozen tissue section (21).

FIG. 15B shows the DNA library obtained from the method and quantified for sequence analysis using a bio-analyzer (12).

Figure 3:
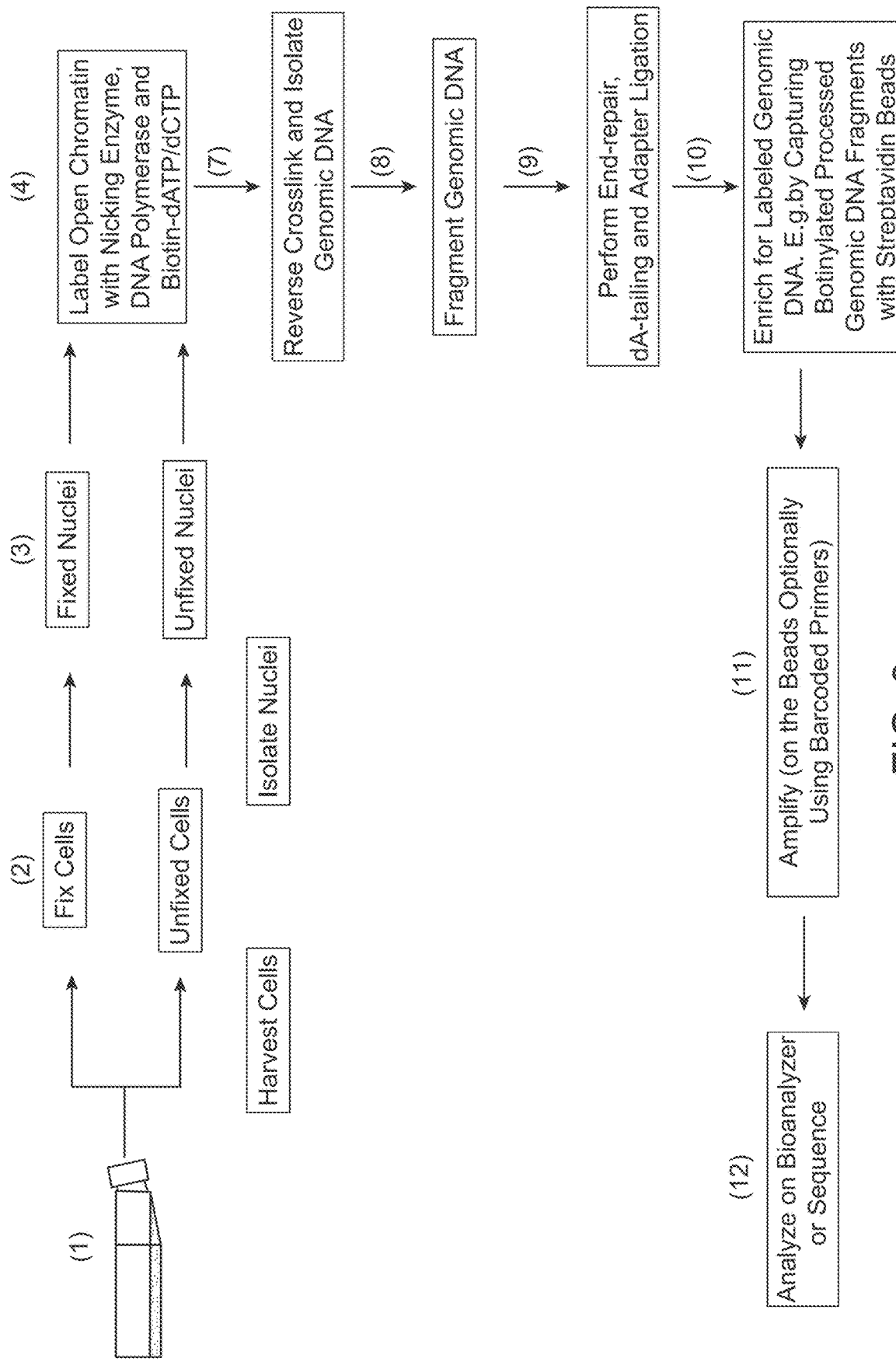
FIG. 3 is a flow diagram showing an embodiment of the method that involves reverse crosslinking the labeled open chromatin and isolating the genomic DNA for next generation DNA sequencing library preparation. Cultured cells, harvested from a flask (1) were either fixed in a preservative, e.g., formaldehyde or remain unfixed (2) so that the nuclei are either fixed or unfixed (3). The nuclei were then labeled using a nicking enzyme (e.g., Nt. CviPII), a polymerase, 4dNTPs and modified dNTP (Biotin-dATP/dCTP) (4). As noted above, although the combination of biotin-dATP/dCTP is illustrated here, this is not intended to be limiting and references herein to the method illustrated in FIG. 3 are not intended to be limited to the use of biotin-dATP/dCTP. Any one or more affinity labeled dNTPs can be used in the methods of the invention.
Figure 16:
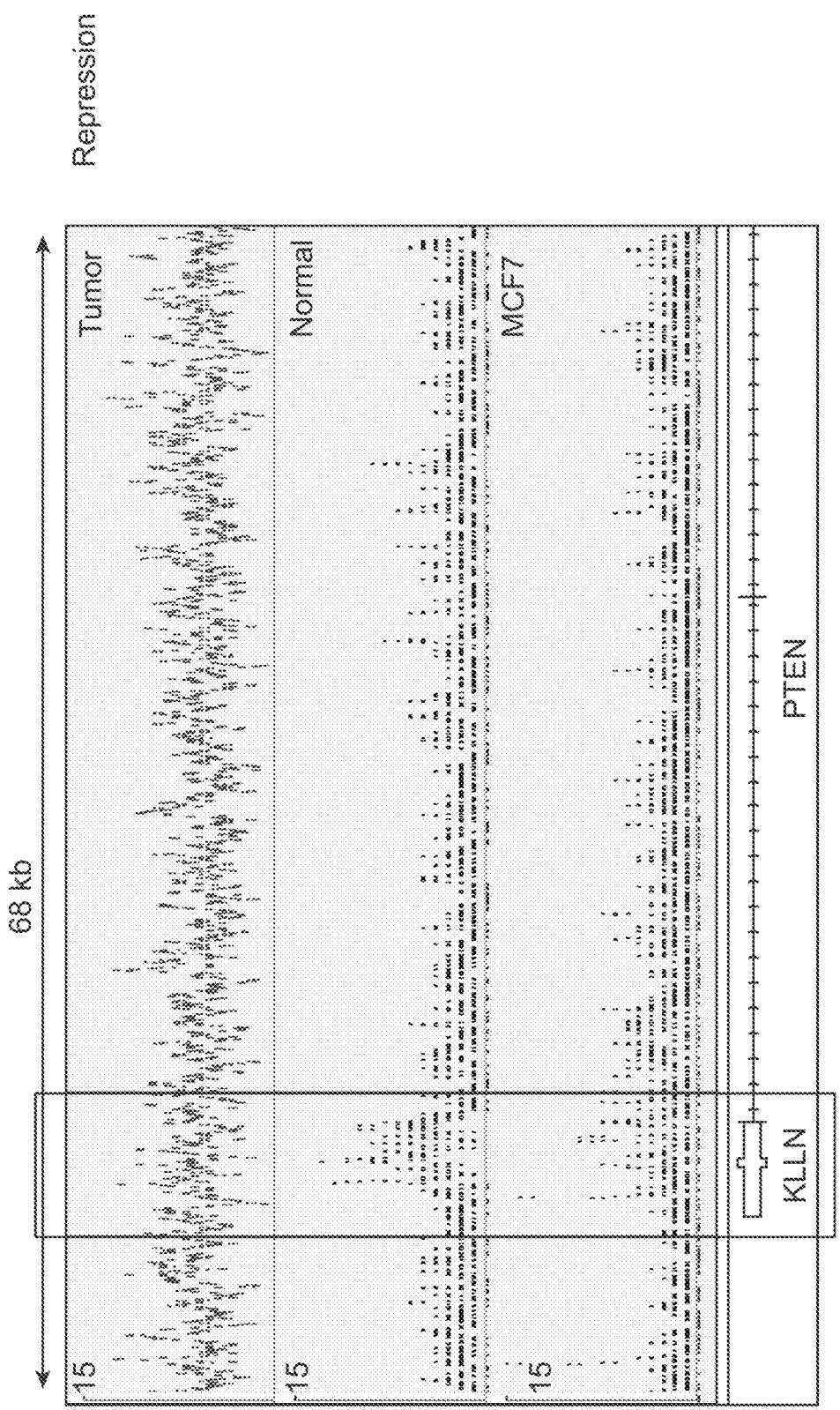

FIG. 16 shows that, using a method that has steps (21)-(23) from FIG. 9 and steps (4) and (7)-(12) in FIG. 3, reliable open chromatin profiling from fresh frozen human breast tissue sections was obtained in a 68 Kb region of the genome. A screenshot of IGV browser showing repression of tumor suppressor gene PTEN in tumor sample as compared to normal and MCF7 cells highlighted using the box around the region.

Figure 17:
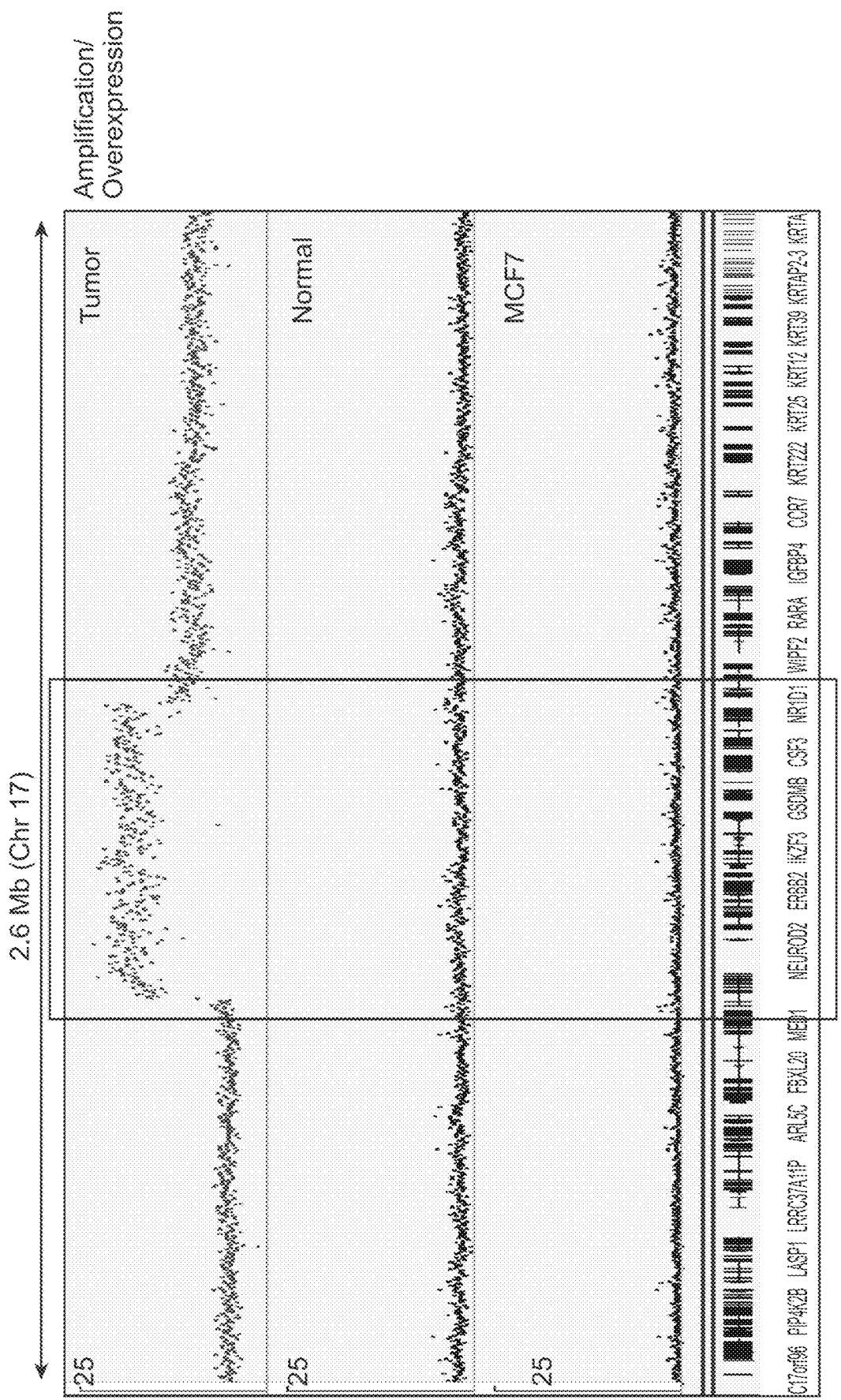

FIG. 17 shows that, using a method that has steps (21)-(23) from FIG. 9 and steps (4) and (7)-(12) in FIG. 3, reliable open chromatin profiling from fresh frozen human breast tissue sections was obtained for a 2.6 MB region of chromosome 17. A screenshot of IGV browser showing amplification/overexpression of ERBB2 locus on chromosome 17 in only tumor sample and not in normal and MCF7 cells highlighted using the box around the region.

Figure 18:
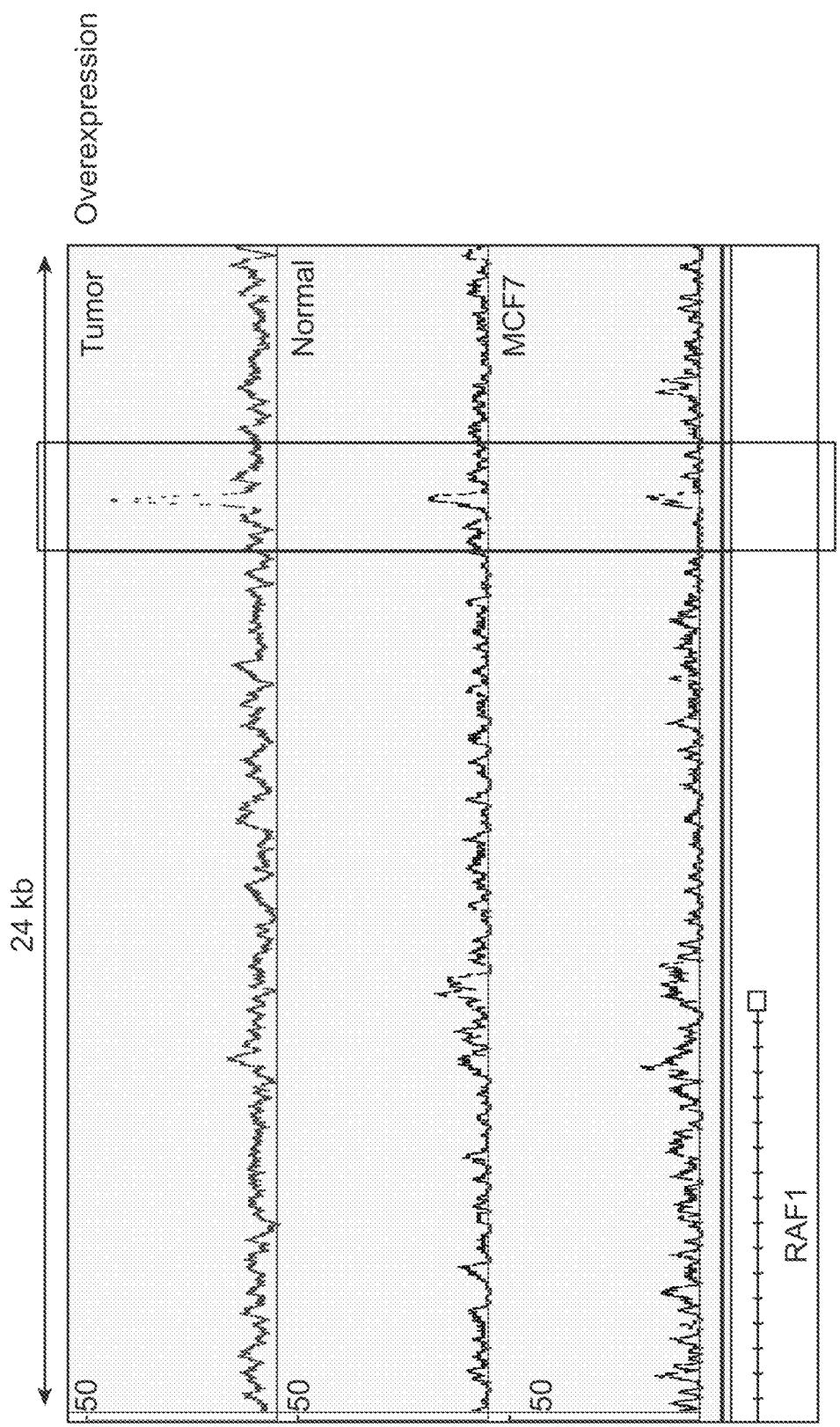

FIG. 18 shows that, using a method that has steps (21)-(23) from FIG. 9 and steps (4) and (7)-(12) in FIG. 3, reliable open chromatin profiling from fresh frozen human breast tissue sections was obtained for a 24 Kb region of the genome. A screenshot of IGV browser showing overexpression of an oncogene, RAF1, in tumor sample as compared to normal and MCF7 cells highlighted using the box around the region.

Figure 19:
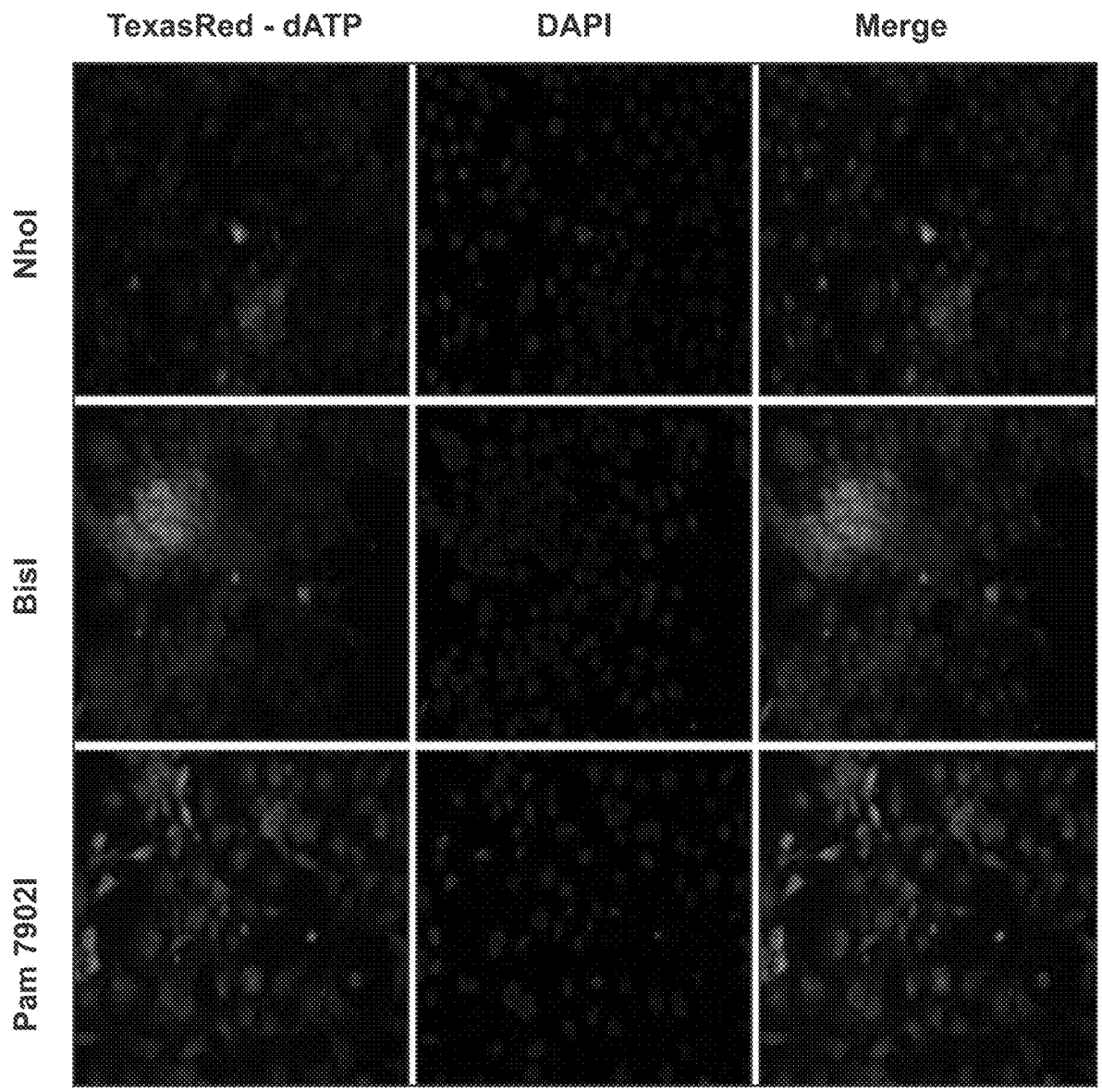

FIG. 19 shows chromatin labeling using nicking enzymes that are specific for methylated chromatin in the nucleus.

The top row of images show results of a labeling reaction performed in the presence of methylspecific nicking enzyme NhoI and DNA polymerase I in the presence of 4×dNTPs and Texas Red-5-dATP (first column). DAPI staining of the same slide is shown in the middle column of this row, and a merge of both is shown in the final column of this row.

The middle row of images show results of a labeling reaction performed in the presence of methylspecific nicking enzyme BisI and DNA polymerase I in presence of 4×dNTPs and Texas Red-5-dATP (first column). DAPI staining of the same slide is shown in the middle column of this row, and a merge of both is shown in the final column of this row.

The bottom row of images show results of a labeling reaction performed in the presence of methylspecific nicking enzyme Pam79021 and DNA polymerase I in presence of 4×dNTPs and Texas Red-5-dATP (first column). DAPI staining of the same slide is shown in the middle column of this row, and a merge of both is shown in the final column of this row.

Figure 20:
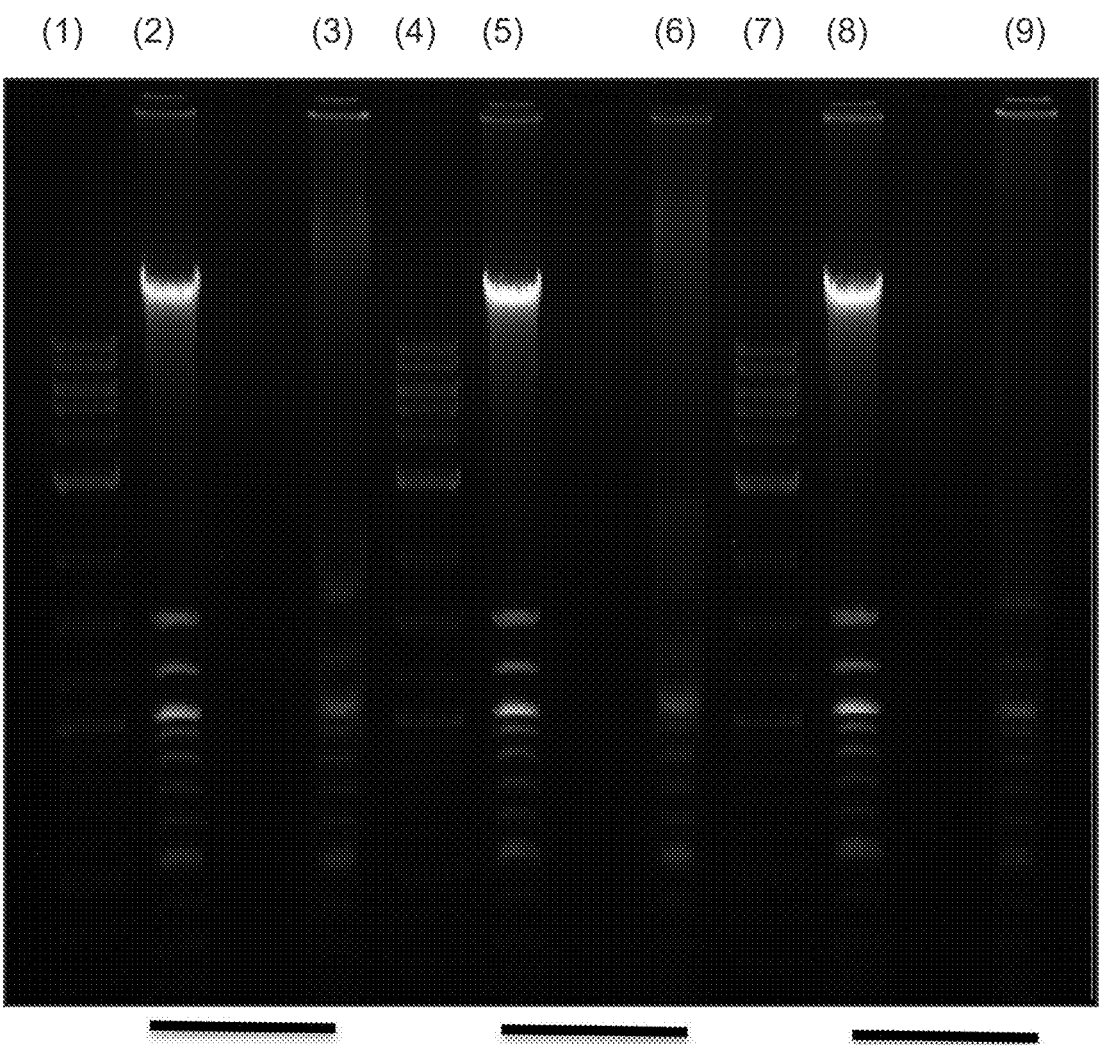

FIG. 20 shows separation of human genome from unmethylated DNA using 5-methylcytosine specific nicking enzymes: Pam 79021 (2-3), NhoI (5-6), and LpnpI (lanes 8-9), in the presence of all dNTPS (dATP, dCTP, dGTP and dTTP) and additionally Biotin-dCTP/dATP.

Input DNA (lanes 2, 5 and 8) is a mixture of human genomic DNA and unmethylated synthetic DNA of various sizes. The bright band on the gel is human DNA and the smaller bands are the synthetic DNA of varying sizes.

Unbound DNA (unlabeled DNA) was obtained after biotin labeled human genomic DNA was removed by streptavidin beads. Lanes 3, 6 and 9 show that using any of the 3 tested nicking enzymes, the human genomic DNA has been removed from the input preparation so that only the synthetic unmethylated DNA remains.

Lanes 1, 4 and 7 are DNA size ladders.

Definitions

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The terms "dNTP mixture" and "four dNTPs" is intended to refer to mixture of deoxyribonucleotides that correspond to G, A, T and C that can be incorporated by a polymerase into a growing polynucleotide strand. A dNTP mix may contain dGTP, dATP, dTTP and dCTP as well as other deoxyribonucleotides, e.g., a labeled dNTP. In one embodiment, the composition of the invention comprises all four dNTPs dGTP, dATP, dTTP and dCTP, and also a labelled dNTP. In one embodiment, the method of the invention uses all four dNTPs dGTP, dATP, dTTP and dCTP, and also a labeled dNTP. In use, the dNTPs may each be at a working concentration of 50 μM to 1 mM (e.g., 100 μM to 500 μM, or 150 μM to 300 μM).

The term "nucleotide" includes dNTPs (also referred to as nucleoside triphosphates) as well as nucleic acid residues that are in a polynucleotide. "Nucleotides" include those moieties that contain not only the known purine and pyrimidine bases, but also other heterocyclic bases that have been modified. Such modifications include methylated purines or pyrimidines, acetylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "methylation-dependent" is intended to refer to an enzyme that only cleaves at, adjacent or proximate to a recognition site in DNA that contains at least one methylated nucleotide, e.g., methylcytosine. These enzymes cleave single strand or double strand DNA depending on whether a subset or all nucleotides (e.g. cytosines) in the recognition site are methylated, and do not cleave DNA if the recognition sequence is unmethylated. Some methylation-dependent nicking enzymes recognize methylated CpGs.

The term "methylation-sensitive" is intended to refer to an enzyme that only nicks at or adjacent to a recognition site that contains one or more unmethylated nucleotides, e.g., one or more unmethylated cytosines. These enzymes nick DNA if one or more nucleotides in the recognition site are unmethylated and do not nick DNA if all the nucleotides in the recognition site are methylated.

The term "methylation-insensitive" is intended to refer to an enzyme that nicks at or adjacent to a recognition site that contains methylated or unmethylated nucleotides (e.g. cytosine or methylcytosine). These enzymes nick DNA regardless of whether any nucleotides in the recognition site are methylated.

A "plurality" contains at least 2 members. For example, a plurality of labeled nucleotides means 2 or more labeled nucleotides. In certain cases, a plurality may have at least 2, at least 5, at least 10, at least 100, at least 1000, at least 10,000, at least 100,000, at least $10^6$, at least $10^7$, at least $10^8$ or at least $10^9$ or more members.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallel sequencing-by-synthesis or sequencing-by-ligation platforms currently employed by Illumina, Life Technologies, Pacific Biosciences and Roche etc. Next-generation sequencing methods may also include nanopore sequencing methods or electronic-detection based methods such as Ion Torrent technology commercialized by Life Technologies.

The term "extending", as used herein, refers to the extension of a nucleic acid strand by the addition of one or more nucleotides using a polymerase. A polymerase may generate an oligonucleotide flap at a nick site in a double stranded DNA where all of one or two types of nucleotides in the flap are labeled. The flap may be a plurality of nucleotides, having a length ranging from 2 nucleotides to several hundred nucleotides. If a primer that is annealed to a nucleic acid is extended, the nucleic acid acts as a template for extension reaction.

The term "in vitro" refers to a reaction that occurs in a vessel with isolated components, not in live cells. The term "ex vivo" refers to a reaction or method that is not performed on the living human or animal body. For example, an ex vivo method may be performed outside the living human or animal body on a sample (e.g. a cell or tissue sample, such as a clinical sample) that has previously been obtained from the human or animal body.

The term "non-naturally occurring" refers to a composition that does not exist in nature. Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" or "variant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an immunologically tag, a detectable fusion partner, such as a fluorescent protein, 3-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state. In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

The term "nicking", as used herein, refers to a reaction that breaks the phosphodiester bond between two nucleotides in one strand of a double-stranded DNA molecule to produce a 3' hydroxyl group and a 5' phosphate group.

The term "nick site," as used herein, refers to the site at which a double-stranded DNA molecule has been nicked.

As used herein, the term "nicking enzyme" refers to a site specific enzyme that cleaves (e.g. nicks) one strand (either the top or bottom strands, but not both strands) of a double-stranded nucleic acid at a nonrandom position in the DNA. In some cases a nicking enzyme will nick the bottom or top strand at a specific sequence on the nucleic acid. Nicking enzymes useful in the compositions and methods of the invention, which may be methylation-dependent, methylation-sensitive, or methylation-insensitive, are known in the art and various examples are provided herein. Nb.BsmI, Nb.BbvCI, Nb.BsrDI, Nb.BtsI, Nt.BbvCI, Nt.AlwI, Nt. CviPII, Nt. BsmAI, Nt. AlwI and Nt.BstNBI are examples of naturally occurring nicking enzymes that are not 5-methyl-cytosine dependent. Nicking enzymes that have been engineered from TypeIIs restriction enzymes (e.g., AlwI, Bpu10I, BbvCI, BsaI, BsmBI, BsmAI, BsmI, BspQI, MlyI, Mva1269I and SapI, etc.) and methods of making nicking enzymes can be found in references for example, U.S. Pat. Nos. 7,081,358; 7,011,966; 7,943,303; 7,820,424.

Labeling of closed chromatin may occur using methylation dependent nicking enzymes that preferably favor $^{5m}$CpG sites. Selective labeling of open chromatin preferentially uses methylation independent or methylation sensitive nicking enzymes, such as exemplified herein. Nicking enzymes that are methylation-dependent include, but are not limited to: NhoI (G5mCNG5mC); BisI (G5mCNG5mC) (Chmuzh, et al., Biotekhnologiya 3: 22-26 (2005); Pam 79021 (G5mCNNG5mC); N.BceSVIII; and Nb.LpnPI (C5mCDG(N)$_{10}$/GGHmC(N)$_{14}$, nicking of the bottom strand) (Cohen Karni, et al., Proc. Natl. Acad. Sci. U.S.A. 108: 11040-11045 (2011); Xu et al, Sci. Rep. 6:28579 (2016)). Methylation-dependent nicking enzymes can be produced using the methods described in, Gutjahr, et al., Nucleic Acids Res. 42:e77 (2014) and Xu, et al., Sci. Rep. 6:28579 (2016). N. Gamma is a strand-specific and site-specific DNA nicking enzyme that cleaves at (YCG4GT or ACtICGR). Nb.LpnPI can be made by making an R335A mutation in the sequence LpnPI sequence defined by Genbank accession number AAU27318.1. Other nicking enzymes can be made by making an Arg to Ala substitution at the position corresponding to position 335 in LpnPI. Such enzymes may cleave at a methylated CpG. The amino acid sequences of N. LpnPI as well as other methylation-specific nicking enzymes is shown below:

N. LpnPI (C$^{5m}$CDG(N)$_{10}$/GGH$^{mC}$(N)$_{14}$)
MKIYSFDTLA NADLIIDAVY EGGSSGNASD DPISKIIKGI GNMGGFRSAG QGIFKKLIVL YTN-MEDGDWP DSIDTSKGQF IYYGDNKHPG HDI-HDTPRQG NATLKMLFDS THNEKDARRI VPPI-FIFVKY PTASSSRSVQ FKGVAVPGYP GLSATDDLIA VWKTTNGQRF QNYRAIFTIL NIPMVSRKWI NSLFDPFGQD NSLNPFYQWK ISGKADVLIA PSTKTIRTQI EQMPRTKLER EILQAVFDYF CEAPIKFEAC AAKIFQLYDE NVLI-DEITRS AVDGGKDAIG RYVLGIKEDP VYAEF-FLEAK CYQPGLNGQN INSVGVKEVS RLIS-RIKNRQ FGVLVTTSFI AKQAYGEVRE DGHPIVFLSG GDISRILIKK GINSTDAVLA WLNSEFSKS (SEQ ID NO:1)

NhoI (G$^{5m}$CWGC)
MNLENLTTRE LLAVSRASLR ELKRRGVIRS GNA-PAGDYAE LLVQRATDGE LANASQKSWD IRTTEGDRLQ VKARVITDEH ANGERQLSTI RSWDFDAAVI VLFDDNFRVW RAARVPAAIM KEAAYYSQHV RGYTVYAKDA LLNHSEVEDW TEQLRSVEQ (SEQ ID NO:2)

BisI (G$^{5m}$CNGC)
MTVSLKKLDD LELTLLYSSL LKELKQRGII RTNNVVGELG EYLAINFYNK TKGLPKLQAA PTGTQNIDAL SIKGDRYSIK TTTGSVTGVF YGMNDPEIRE PDIQKFEYVI IVLFDKEYSL KGI-YELSWES FIKHKRWHKR MRAWNLTITK ALLSDSEIIF EKESKLLN (SEQ ID NO:3)

Pam79021 (G$^{5m}$CNNG$^{5m}$C)
MNMEVQDDVY EILREAKILA RRYYHLTGKP LGVTGEVAEY EVCRILGLEL EQARTAGFDA IETRDGVDLK VQIKGRYFPN SRMRGGRLGS IDLKQPFDIV MLVLLDGDYN AFQIFEAQRP DVEAILTRPG SKSRNERGAV GISQFKAISI LRW-EREGVDQ PA (SEQ ID NO:4)

A description of nicking enzymes can be found in a variety of publications (e.g., Bellamy, et al. J. Mol. Biol. 2005 345, 641-653; Heiter, et al., J. Mol. Biol. 2005 348, 631-640; Xu, et al., Proc. Natl. Acad. Sci. USA 200198, 12990-12995; Samuelson, et al., Nucl. Acids Res. 2004 32, 3661-3671; Zhu, et al., J. Mol. Biol. 2004 337, 573-583; Morgan, et al., Biol. Chem. 2000 381, 1123-1125; Chan, Nucl. Acids Res. 2004 32, 6187-6199; Sasnauskas, Proc. Natl. Acad. Sci. USA 2003 100, 6410-6415; Jo, et al., PNAS 2007 104:2673-2678; Xiao, et al., Nucleic Acids Res. 2007

35:e16; U.S. Pat. Nos. 7,081,358; 6,191,267, US 2005/0136462, U.S. Pat. Nos. 7,943,303, 8,163,529, WO 2006/047183 and WO 2008/0268507. DNase I is not a nicking enzyme because DNase I cleaves DNA at random positions. Thus, as used herein, the term nicking enzyme specifically excludes DNase I.

A nicking enzyme can also be made by inactivating one of the catalytic domains. For example see U.S. Pat. No. 7,081,358. Another type of example is a programmable endonuclease, e.g., Cas9 or a functional equivalent thereof (such as Argonaute or Cpf1). For example, Cas9 contains two catalytic domains, RuvC and HNH. Inactivating one of those domains will generate a nicking enzyme. In Cas9, the RuvC domain can be inactivated by an amino acid substitution at position D10 (e.g., D10A) and the HNH domain can be inactivated by an amino acid substitution at position H840 (e.g., H840A), or at a position corresponding to those amino acids in other proteins. Such endonucleases may be Argonaute or Type II CRISPR/Cas endonucleases that are composed of two components: a nuclease (e.g., a Cas9 or Cpf1 endonuclease or variant or ortholog thereof) that cleaves the target DNA and a guide nucleic acid e.g., a guide DNA or RNA that targets the nuclease to a specific site in the target DNA (see, e.g., Hsu, et al., Nature Biotechnology 2013 31: 827-832). A nicking enzyme can also be made by fusing a site specific DNA binding domain such as the DNA binding domain of a DNA binding protein (e.g., a restriction endonuclease, a transcription factor, or another domain that binds to DNA at non-random positions) with a nuclease or deaminase so that it acts on a non-random site. In these embodiments, the deaminase can introduce a uracil, and a nick can be created by removing the uracil using a deglycosylase and treating the abasic site with an AP endonuclease. It will be understood from the foregoing that non-random cleavage by a nicking enzyme results from recognition sites within the nicking enzyme or from guide molecules that direct the nicking enzyme to a non-random site or optionally by inherent defined bias of the enzyme for a plurality of nucleotides that may be preferentially As and Ts or Gc and Cs.

As used herein, the term "chromatin" refers to a complex of molecules including proteins and genomic DNA as found in a nucleus of a eukaryotic cell. Chromatin is composed in part of histone proteins that form nucleosomes, genomic DNA, and other DNA binding proteins (e.g., transcription factors) that are bound to the genomic DNA. Chromatin is therefore distinct from purified genomic DNA. Chromatin is available in permeabilized cells, in isolated nuclei, and as well as in isolated chromatin.

As used herein, the terms "open chromatin" and "closed chromatin" refer to the level of the accessibility of genomic DNA in a sample that contains chromatin. Open chromatin (or "euchromatin") is not densely packed into nucleosomes and can be accessed by a nicking enzyme; it is accessible chromatin. In contrast, closed chromatin (or "heterochromatin") is densely packaged into nucleosomes and not accessible by a nick endonuclease. Open and closed chromatins are schematically illustrated in FIG. 1.

As used herein, the term "isolated nucleus" refers to a nucleus that has been isolated from other components of a cell, e.g., from the cytoplasm and plasma membrane, by centrifugation or another technique.

As used herein, the term "permeabilized cell" refers to a cell that has a cell plasma membrane and, in some cases a nuclear membrane, that have been permeabilized, e.g., by a detergent.

As used herein, the term "fixed cell" refers to a cell that has been treated with a crosslinking or non-crosslinking fixative, e.g., formaldehyde or paraformaldehyde, acetone, or methanol or the like. In some embodiments, a fixed cell may be "formalin fixed", in which case it may be fixed in formaldehyde (e.g., 3%-5% formaldehyde in phosphate buffered saline) or Bouin solution. An "unfixed" cell refers to a cell that has not been treated by such an agent.

As used herein, the term "labeled nucleotide" refers to a modified nucleotide that has an optically detectable label or an affinity tag attached thereto.

As used herein, the term "optically detectible label" refers to a light-emitting or fluorescent label that can be detected using a light detector, e.g., a microscope. Light emitting labels include fluorophores, although others are known.

As used herein, the term "affinity tag" refers to a tag that can be used to separate a molecule to which the affinity tag is attached from other molecules that do not contain the affinity tag. In many cases, an affinity tag is a member of a specific binding pair, i.e. two molecules where one of the molecules through chemical or physical means specifically binds to the other molecule. The complementary member of the specific binding pair, which can be referred to herein as a "capture agent" may be immobilized (e.g., to a chromatography support, a bead or a planar surface) to produce an affinity chromatography support that specifically binds the affinity tag. Affinity tags include a biotin moiety (e.g., biotin, desthibiotin, oxybiotin, 2-iminobiotin, diaminobiotin, biotin sulfoxide, biocytin, etc.) which can bind to streptavidin. Affinity tags also include chemoselective groups such as azido and alkynyl groups, which can participate in a copper-free cycloadition reaction (see, e.g., Kolb, et al., Drug Discov Today 2003 8: 1128-113 and Baskin, et al., Proc. Natl. Acad. Sci. 2007 104: 16793-16797).

As used herein, the term "enriching" refers to a method step in which some components of a sample (e.g., components that are tagged) are separated from other components in the sample (e.g., components that are not tagged).

The term "barcode sequence", "molecular barcode" or "index", as used herein, refers to a unique sequence of nucleotides used to (a) identify and/or track the source of a polynucleotide in a reaction and/or (b) count how many times an initial molecule is sequenced (e.g., in cases where substantially every molecule in a sample is tagged with a different sequence, and then the sample is amplified). A barcode sequence may be at the 5'-end, the 3'-end or in the middle of an oligonucleotide, or both the 5' end and the 3' end. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker, et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

The term "reacting," as used herein, refers to combining under conditions (e.g., a suitable temperature, time and conditions) that result in a reaction, e.g., nicking and/or strand extension by a polymerase.

The term "NE-seq" refers to embodiments in which nuclei are examined for open chromatin by adding a nicking enzyme to the nuclei, permitting open chromatin to be nicked, and with a strand-displacing polymerase having activity, causing a plurality of labeled nucleotides to be incorporated at the nick site by newly synthesized strand, enrichment of the labeled polynucleotides, followed by library construction, amplification, and sequencing.

Other definitions of terms may appear throughout the specification.

DESCRIPTION OF EXEMPLARY EMBODIMENTS

As noted above, a composition comprising a nicking enzyme, a polymerase, four dNTPs and at least one labeled dNTP is provided for sequencing of open chromatin. The composition may alternatively comprise a mixture of a nicking enzyme, four dNTPs, and at least one labeled dNTP. In one embodiment, therefore, the polymerase is provided separately from the nicking enzyme, dNTPs, and at least one labelled dNTP (e.g. in a separate composition). A nicking enzyme may be provided for visualizing open chromatin in a histological preparation of a cell biopsy. In one embodiment, therefore, the composition is for visualizing open chromatin in a histological preparation of a tissue biopsy. In one embodiment, the composition is for detecting open chromatin. In one embodiment, the composition is for analyzing chromatin. In some embodiments, the components of the composition may be dissolved in an aqueous solution that may comprise a buffering agent, such as a non-naturally occurring buffering agent, and other essential compounds required for activity of the enzymes in the composition. The composition may contain other components, e.g., glycerol. The concentration of the one or more labeled dNTP in the composition may be in the range of 3 µM or 5 µM to 200 µM. In any embodiment, the nicking enzyme may be methylation-sensitive or methylation-dependent. In some embodiments, the molar ratio of the labeled dNTP to the unlabeled version of the same dNTP (e.g. biotin-dCTP to dCTP) in the composition may be in the range of 1:1000 to 1000:1, e.g., 1:100 to 100:1 or 1:10 to 10:1. For example, the ratio the molar ratio of the labeled dNTP to the corresponding unlabeled dNTP (e.g. biotin-dCTP to dCTP) in the nucleotide mix may be in the range of 1:1000 to 1:100, 1:100 to 1:10, 1:10 to 1:1, 1:1 to 1:10, 1:10 to 1:100, or 1:100 to 100:1000.

The nicking enzyme used in some embodiments of the method may be from any source and, in some embodiments, a plurality of nicking enzymes may be used. Examples are provided above for analyzing open chromatin or closed chromatin.

The polymerase employed in the method may be a nick translation polymerase. Nick translation occurs when the polymerase associated flap endonuclease chews up one strand of the DNA as the polymerase progresses in the 5'-3' direction, essentially replacing the existing DNA strand. Strand displacement displaces the strand ahead of the replication fork without destroying it. Either activity could be employed here. DNA Polymerase I, Taq, and the wild type Bst DNA polymerase have a 5'-3' flap endonuclease activity and will do nick translation. Phi29 or Klenow fragment or Bst large fragment would do strand displacement. T4 and T7 DNA polymerases have neither strand displacement or nick translation abilities, but can be used in the chewback/fill-in approach described here. The polymerase and nick translation move in the 5' to 3' direction starting from a nick site. Alternatively, the polymerase could be a proofreading polymerase that removes one or more nucleotides in the 3' to 5' direction starting from a nick site, and then fills in the overhang it has just generated. As such, the polymerase may or may not have strand displacement activity. In one embodiment, the polymerase is a strand-displacing polymerase. Examples of strand-displacing polymerases are known in the art. Any enzyme known in the art capable of incorporating naturally-occurring nucleotides, nucleotides base analogs, or combinations thereof into a polynucleotide may be utilized in accordance with the present disclosure. Non-limiting examples of DNA polymerases useful in the invention include *E. coli* DNA polymerase I, *E. coli* DNA polymerase I Large Fragment (Klenow fragment), phage T4 DNA polymerase, or phage T7 DNA polymerase. The polymerase can be a thermophilic polymerase such as *Thermus aquaticus* (Taq) DNA polymerase, *Thermus flavus* (Tfl) DNA polymerase, *Thermus thermophilus* (Tth) DNA polymerase, *Thermococcus aggregans* (Tag) DNA polymerase, *Thermococcus litoralis* (Tli) DNA polymerase, *Pyrococcus furiosus* (Pfu) DNA polymerase, Vent DNA polymerase, or *Bacillus stearothermophilus* (Bst) DNA polymerase.

The one or more labeled dNTPs in the composition may vary. For example, in some embodiments, the composition may comprise any one or combination of labeled dGTP, labeled dATP, labeled dTTP, and labeled dCTP. In one embodiment, the composition comprises a combination of labeled dATP and labeled dCTP. In some embodiments, the labeled nucleotides could be chain terminator nucleotides. In one embodiment, the labeled dNTP comprises an affinity tag. If the labeled dNTP comprises an affinity tag, then the affinity tag may comprise an azide/alkyne group (which are suitable for conjugation to another moiety, e.g., a solid support via click chemistry), or a biotin group so that the labeled nucleic acid can be enriched on a suitable support and sequenced.

In one embodiment, the labeled dNTP comprises an optically detectable label. If the labeled dNTP comprises an optically detectable label, the label may comprise a fluorophore (or any other type of optically detectable moiety). Fluorophores of interest include xanthene dyes, e.g. fluorescein and rhodamine dyes, such as fluorescein isothiocyanate (FITC), 6-carboxyfluorescein (commonly known by the abbreviations FAM and F),6-carboxy-2',4',7',4,7-hexachlorofluorescein (HEX), 6-carboxy-4', 5'-dichloro-2', 7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc.; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy3, and Cy5, etc. (Amersham Inc., Piscataway, NJ). Suitable fluorescent labels may be listed in Kricka, et al., *Ann Clin Biochem.* 39:114-29, 2002. Such nucleotides are commercially available from a variety of vendors.

In any embodiment in which the composition comprises a cell, the cell may be permeabilized to allow access of the other components of the composition to the chromatin. The permeabilization can be performed in a way to minimally perturb the nuclei in the cell sample. In some instances, the cells can be permeabilized using a permeabilization agent. Examples of permeabilization agents include, but are not limited to, NP40, digitonin, tween, streptolysin, and cationic lipids. In other instances, the cell sample can be permeabilized using hypotonic shock and/or ultrasonication.

Figure 1B:
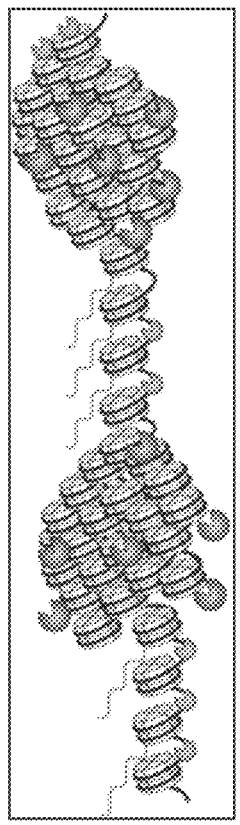
Figure 1C:
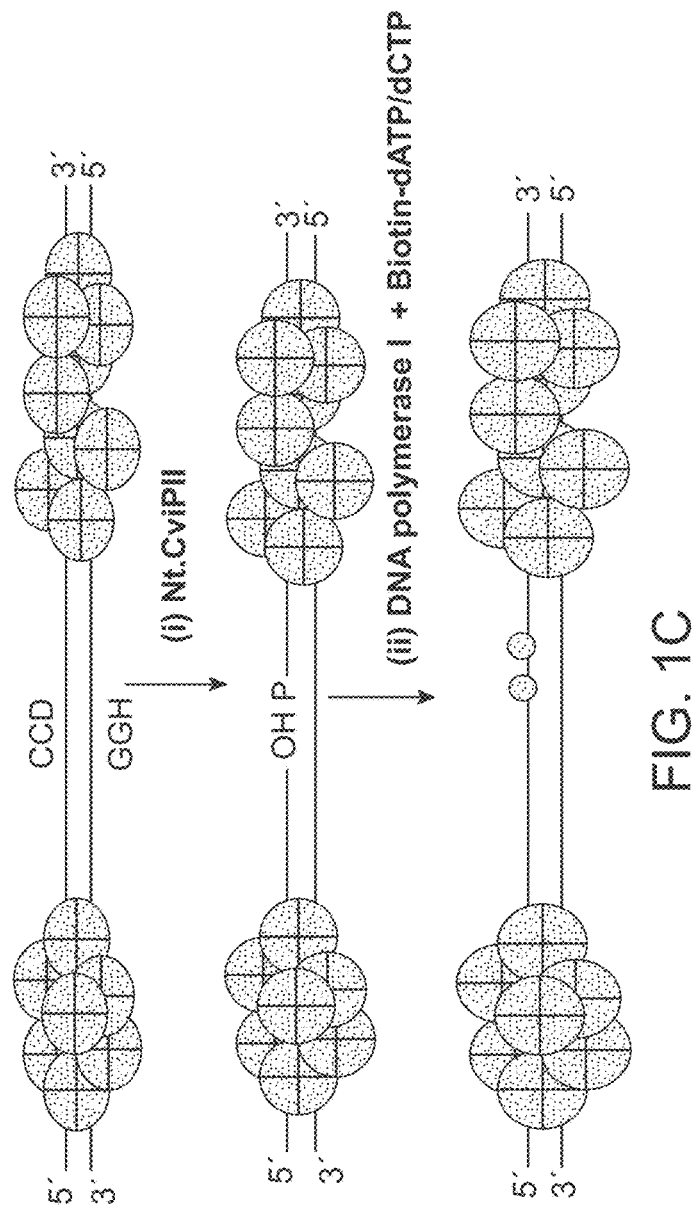
Figure 2A:
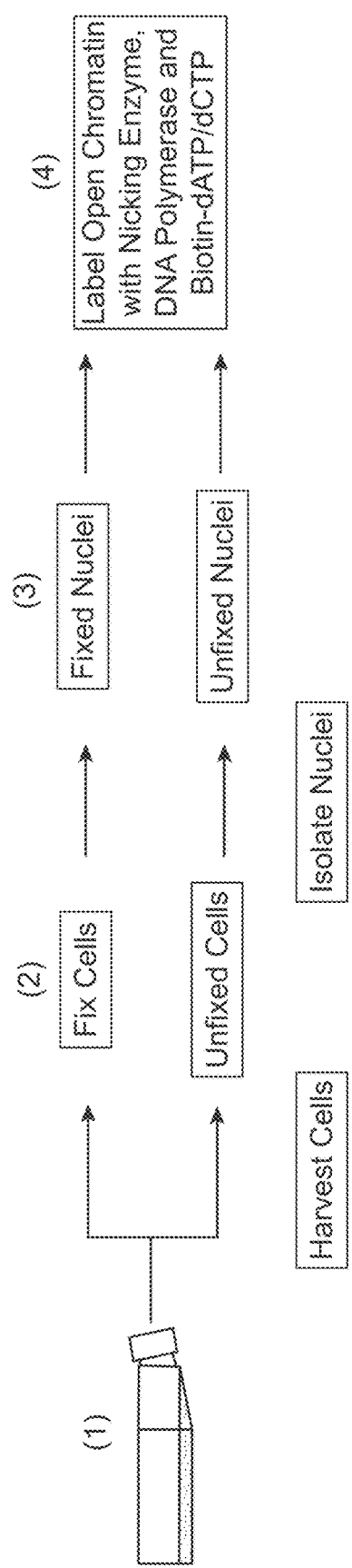
FIG. 2A-2B shows a flow diagram for an embodiment of the method of labeling open chromatin as well as an example of results obtainable from the method using a DNA dot blot.
Figure 2B:
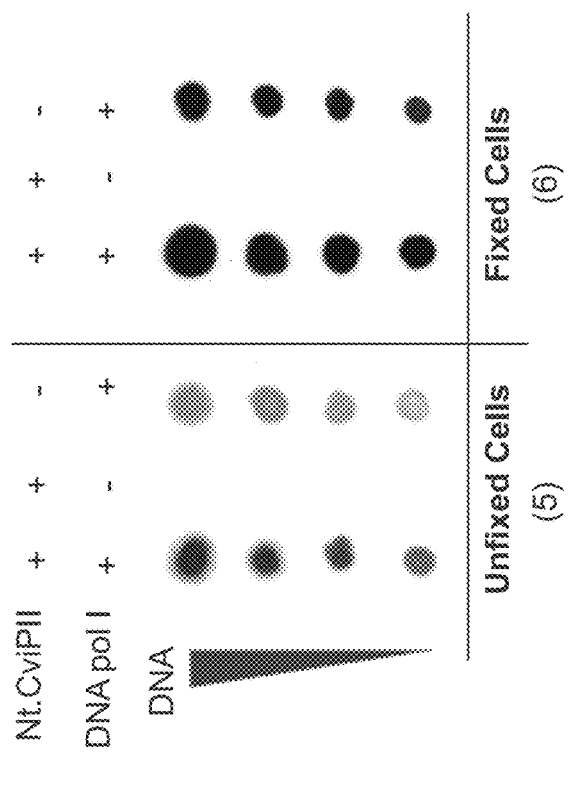

An overview of an embodiment of the method is shown in FIG. 1A-1C. The nicking enzyme Nt.CviPII, DNA polymerase I, and combination of biotin-dATP/dCTP illustrated in FIG. 1A-1C are not intended to be limiting, and any nicking enzyme, polymerase, and labelled dNTP(s) described herein may be used in the method of the invention. FIG. 2A-2B shows that the method works with nuclei obtained both fixed and unfixed cells.

The minimum number of cells that can be used in the method is 10, e.g., in some embodiments the number of cells that can be used in the method is as few as 25 cells or more, as few as 50 cells or more, at least 50, at least 100, or at least 250 cells. In certain embodiments, the sample comprises fewer than 500 cells, fewer than 250 cells, fewer than 200 cells, fewer than 100 cells, fewer than 50 cells, or fewer than 25 cells. In some embodiments, therefore, the method is performed on chromatin obtained from as few as 1, 5, 10, 25, 50, 100 or 250 cells. In certain embodiments, the chromatin in the sample is from fewer than 500 cells, fewer than 250 cells, fewer than 200 cells, fewer than 100 cells, fewer than 50 cells, or fewer than 25 cells. In certain embodiments, chromatin from a single cell may be analyzed.

If the sample is going to be imaged, then the sample may be optionally stained with other antibodies/stains before imaging. In some embodiments, the stain may enhance contrast or imaging of intracellular or extracellular structures. For example, the sample may be stained with DAPI, ethidium bromide, Hoechst 33258, Hoechst 33342, eosin, hematoxylin, methylene blue, or rhodamine. In some embodiments, the sample may be stained with DAPI. In some embodiments, the sample may be stained with haematoxylin and eosin (H&E). In some embodiments, the tissue sections may be immunohistochemically stained using standard protocols and optimized as necessary for each primary antibody, using standard processes. Examples of markers that can be investigated in these embodiments (e.g., ER, PR, Ki-67, and HER2 etc.) are well known. An example of one implementation of such a method is shown in FIG. 9 (wherein the use of Texas Red-5-dATP/dCTP is not intended to be limiting, and can be replaced by any other optically-detectably labeled nucleotides). In these embodiments, the optically detectable label can be detected using any suitable means. For example, fluorescence can be viewed with a fluorescence microscope and an appropriate filter for each fluorophore, or by using dual or triple bandpass filter sets to observe multiple fluorophore (See, e.g., U.S. Pat. No. 5,776,688). After the images have been obtained, the images may be overlaid or compared and analyzed to identify the boundaries of individual cells, and/or subcellular features in individual cells, in the image. In alternative embodiments, the stained cells could be analyzed by flow cytometry (e.g., FACS).

If the tagged DNA is going to be sequenced, then the sample may be processed using the method shown in FIG. 3 (wherein the use of biotin-dATP/dCTP and streptavidin beads is not intended to be limiting, and can be replaced by any other affinity-tagged nucleotides and corresponding capture moiety, optionally linked to a solid phase, not limited to a bead). Thus, in one embodiment, after labelling the open chromatin using the method described herein, the method comprises reverse cross-linking and isolating labelled genomic DNA, and then fragmenting the isolated labelled genomic DNA. The reverse crosslinking may be done using heat or by chemical treatment, and genomic DNA may be fragmented to any convenient size (e.g., a median size in the range of 100 bp to 1 kb, e.g., 150 bp to 500 bp). The method may further comprise processing the labelled genomic DNA fragments by performing end repair, dA-tailing, and/or adapter ligation, which may be done using conventional methods. Any of the adaptors and/or primers may carry a barcode to facilitate multiplexing and/or molecular counting. The method then comprises enriching the labeled genomic DNA using any convenient method—e.g. by capturing the labelled, processed genomic DNA fragments. For example, if the label is a biotin moiety (as described herein), the labelled, processed genomic DNA fragments may be enriched by capturing using a streptavidin-coated solid phase such as a streptavidin-coated bead. The enriched DNA may then be amplified using any convenient method. The enriched DNA is then analyzed and/or sequenced. As would be apparent, the enriched sequences may be sequenced using any convenient method. For example, the fragments may be sequenced using Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method, etc. Examples of such methods are described in the following references: Margulies, et al., Nature 2005 437: 376-80; Ronaghi, et al., Analytical Biochemistry 1996 242: 84-9; Shendure, Science 2005 309: 1728; Imelfort, et al., Brief Bioinform. 2009 10:609-18; Fox, et al., Methods Mol Biol. 2009; 553:79-108; Appleby, et al., Methods Mol Biol. 2009; 513:19-39; English, PLoS One. 2012 7: e47768; and Morozova, Genomics. 2008 92:255-64, which are incorporated by reference for the general descriptions of the methods and the particular steps of the methods, including all starting products, reagents, and final products for each of the steps.

In some embodiments, the sequence read obtained from the sequencing step may be mapped onto a genomic sequence to obtain a map of the open and closed chromatin. In some cases, an abundant sequence indicates that the region corresponding to that sequence is in open chromatin. Such a map can show one or more of the following: a profile of chromatin accessibility along a region; DNA binding protein (e.g., transcription factor) occupancy for a site in a region; nucleosome-free DNA in a region; positioning of nucleosomes along a region; or a profile of chromatin states along a region, for example. In certain instances, the map can also be annotated with sequence information, and information about the sequence (e.g., the positions of promoters, introns, exons, known enhancers, transcriptional start sites, untranslated regions, terminators, etc.) so that the chromatin accessibility map can be viewed in context with the annotation.

The nuclei containing chromatin can be from any source. In certain cases, the nuclei may be obtained from a culture of cells, e.g., a cell line. In other cases, the cells may be isolated from an individual (e.g., a patient). The cells may be isolated from a soft tissue or from a bodily fluid, or from a cell culture that is grown in vitro. In particular embodiments, the nuclei may be isolated from a soft tissue such as brain, adrenal gland, skin, lung, spleen, kidney, liver, spleen, lymph node, bone marrow, bladder, stomach, small intestine, large intestine or muscle, etc. Bodily fluids include blood, plasma, saliva, mucous, phlegm, cerebral spinal fluid, pleural fluid, tears, lacteal duct fluid, lymph, sputum, cerebrospinal fluid, synovial fluid, urine, amniotic fluid, and semen, etc. In some embodiments, the chromatin may from a tissue biopsy obtained from a patient. Biopsies of interest include both tumor and non-neoplastic biopsies of skin (melanomas, carcinomas, etc.), soft tissue, bone, breast, colon, liver, kidney, adrenal, gastrointestinal, pancreatic, gall bladder, salivary gland, cervical, ovary, uterus, testis, prostate, lung, thymus, thyroid, parathyroid, pituitary (adenomas, etc.), brain, spinal cord, ocular, nerve, and skeletal muscle, etc.

In some embodiments, the chromatin analyzed in the method may be from blood cells, wherein "blood cells" refers to a sample of whole blood or a sub-population of cells in whole blood. Sub-populations of cells in whole blood include platelets, red blood cells (erythrocytes), platelets and white blood cells (i.e., peripheral blood leukocytes, which are made up of neutrophils, lymphocytes, eosinophils, basophils and monocytes). These five types of white blood cells can be further divided into two groups, granulocytes (which are also known as polymorphonuclear leukocytes and include neutrophils, eosinophils and basophils) and mononuclear leukocytes (which include monocytes and lymphocytes). Lymphocytes can be further divided into T cells, B cells and NK cells. Peripheral blood cells are found in the circulating pool of blood and not sequestered within the lymphatic system, spleen, liver, or bone marrow. Other cells are present in blood that can be isolated. If blood is first contacted with an agent and then a sample of the blood is used in an assay, then a portion or all of the contacted blood may be used in the assay.

In certain embodiments, the cell sample can be isolated directly from a primary source. For example, the cell sample can be isolated directly from fresh tissues. In other cases, the cell sample can be isolated directly from frozen tissues. In yet other cases, the cell sample can be isolated directly from fixed tissues.

Using the methods provided in the present disclosure, the disease state in a subject can be analyzed.

In some embodiments, the method can be used to compare two samples to identify a change in chromatin structure. In these embodiments, the method may comprise analyzing a first population of cells using the above-described method to produce a data set and optionally a first epigenetic map; and analyzing a second population of cells using the above-described method to produce a second data set and optionally a second epigenetic map; and comparing the first data set or epigenetic map to the second data set or epigenetic map, e.g., to see if there are any changes in chromatin openness or transcription factor occupancy, for example.

In some embodiments, the first population of cells and the second population of cells may be collected from the same individual at different times. In other embodiments, the first population of cells and the second population of cells are different populations of cells collected from tissues or different individuals.

Exemplary cell types that can be used in the method include, for example, cells isolated from a tissue biopsy (e.g., from a tissue having a disease such as colon, breast, prostate, lung, skin cancer, or infected with a pathogen etc.) and normal cells from the same tissue, e.g., from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and normal cells (e.g., cells that are otherwise identical to the experimental cells except that they are not immortalized, infected, or treated, etc.); cells isolated from a mammal with a cancer, a disease, a geriatric mammal, or a mammal exposed to a condition, and cells from a mammal of the same species, e.g., from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be compared. In another embodiment, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells. Cells from yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used.

In some exemplary embodiments, the method may be used to identify the effect of a test agent, e.g., a drug, or to determine if there are differences in the effect of two or more different test agents. In these embodiments, two or more identical populations of cells may be prepared and, depending on how the experiment is to be performed, one or more of the populations of cells may be incubated with the test agent for a defined period of time. After incubation with the test agent, the chromatin of the populations of cells can be analyzed using the methods set forth above, and the results can be compared. In a particular embodiment, the cells may be blood cells, and the cells can be incubated with the test agent ex vivo. These methods can be used to determine the mode of action of a test agent, to identify changes in chromatin structure or transcription factor occupancy in response to the drug, for example.

The method described above may also be used as a diagnostic (which term is intended to include methods that provide a diagnosis as well as methods that provide a prognosis). Diagnostic and prognostic methods may be performed ex vivo, on a sample of chromatin obtained from a subject or patient. These methods may comprise, e.g., analyzing chromatin from a patient using the method described above to produce results; and providing a diagnosis or prognosis based on the results.

The method set forth herein may be used to provide a reliable diagnostic to any condition associated with altered chromatin. The method can be applied to the characterization, classification, differentiation, grading, staging, diagnosis, or prognosis of a condition characterized by a chromatin alteration. For example, the method can be used to determine whether the chromatin in a sample from an individual suspected of being affected by a disease or condition is the same as or different to a sample that is considered "normal" with respect to the disease or condition. In particular embodiments, the method can be directed to diagnosing an individual with a condition that is characterized by altered chromatin at a particular locus in a test sample, where the pattern is correlated with the condition. The methods can also be used for predicting the susceptibility of an individual to a condition.

Exemplary conditions that are suitable for analysis using the methods set forth herein can be, for example, cell proliferative disorder or predisposition to cell proliferative disorder; metabolic malfunction or disorder; immune malfunction, damage or disorder; CNS malfunction, damage or disease; symptoms of aggression or behavioral disturbance; clinical, psychological and social consequences of brain damage; psychotic disturbance and personality disorder; dementia or associated syndrome; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, the muscles, the connective tissue or the bones; endocrine and metabolic malfunction, damage or disease; headache or sexual malfunction, and combinations thereof.

In some embodiments, the method can provide a prognosis, e.g., to determine if a patient is at risk for recurrence. Cancer recurrence is a concern relating to a variety of types of cancer. The prognostic method can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The method can also be used to determining a proper course of treatment for a patient having a disease or condition, e.g., a patient that has cancer. A course of treatment refers to the therapeutic measures taken for a patient after diagnosis or after treatment. For example, a determination of the likelihood for recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

In a particular embodiment, a lab will receive a sample (e.g., blood) from a remote location (e.g., a physician's office or hospital), the lab will analyze cells in the sample as described above to produce data, and the data may be forwarded to the remote location for analysis.

Nicking enzymes used in the methods described above for epigenome analysis, may also be used to differentiate eukaryotic DNA from prokaryotic DNA including mitochondria and chloroplast DNA. This can be achieved by relying on the substantially greater density of methylated nucleotides in eukaryotic DNA than in prokaryotic DNA.

In one embodiment, a nicking enzyme that has a specificity for a recognition site that contains $^{5m}$CpG such as Pam 7902 I, LpnI, MspJI (New England Biolabs, Ipswich, MA), NhoI and BisI can be used on DNA in a body fluid or cells from an invertebrate (such as a mosquito) or vertebrate (such as a human) for introducing labeled nucleotides into the methylated DNA so that it can be enriched by binding to an affinity matrix if the label is an affinity tag such as biotin. Unmethylated prokaryotic DNA will be substantially unlabeled and thus will not bind the affinity column and can be separated from the eukaryotic DNA in the eluent.

In one embodiment, human DNA can be separated from microbial sequences in body fluid and tissue samples (such as saliva, feces, etc.) for mutation, epimutation and genomics analysis. Obtaining saliva for genomic analyses is a popular collection method with less invasiveness compared to blood draws or biopsies. However, a major drawback of saliva DNA is the non-human DNA contamination particularly of oral microbiome. A $^{5m}$C specific nicking enzyme (e.g. Pam 7902 I, NhoI, N. LpnpI, BisI and MspJI) is used to label human genome (for example, with biotin) (see for example FIG. 20) which is then enriched (for example, using streptavidin beads) for sequence analysis. In some embodiments, the analysis of chromatin is performed on isolated nuclei. Therefore, amounts of mitochondrial DNA are minimal at the starting point of the method. If the frequency of nicking enzyme recognition sites (e.g. CCD sites) in the mitochondrial DNA is very high and the DNA is devoid of histones, any residual mitochondrial DNA would be substantially fragmented.

EMBODIMENTS

Embodiment 1. A composition comprising: a nicking enzyme, a polymerase and a labeled nucleotide.

Embodiment 2. The composition of embodiment 1, further comprising chromatin.

Embodiment 3. The composition of embodiment 2, wherein the chromatin comprises open chromatin and closed chromatin, and at least some of the open chromatin is labeled by the labeled nucleotide.

Embodiment 4. The composition of any of embodiments 2-3, wherein the composition comprises an isolated nucleus, and the chromatin is contained within an isolated nucleus.

Embodiment 5. The composition of any of embodiments 2-3, wherein the composition comprises a permeabilized cell, wherein the chromatin is contained in the permeabilized cell.

Embodiment 6. The composition of embodiment 5, wherein the cell is a fixed cell.

Embodiment 7. The composition of embodiment 5, wherein the cell is an unfixed cell.

Embodiment 8. The composition of any of embodiments 5-7, wherein the composition comprises a clinical sample, wherein the cell is in the clinical sample.

Embodiment 9. The composition of embodiment 8, wherein the clinical sample is a tumor biopsy.

Embodiment 10. The composition of any prior embodiment, wherein the labeled nucleotide comprises a detectable label.

Embodiment 11. The composition of any prior embodiment, wherein the detectable label is a fluorophore.

Embodiment 12. The composition of any of embodiments 1-9, wherein the labeled nucleotide comprises an affinity tag.

Embodiment 13. The composition of embodiment 12, wherein the labeled nucleotide comprises a biotin moiety.

Embodiment 13.1. The composition of any prior embodiment, wherein the nicking enzyme is methylation-dependent.

Embodiment 13.2. The composition of any prior embodiment, wherein the nicking enzyme is methylation-sensitive.

Embodiment 14. A method for detecting open chromatin, comprising: (a) obtaining a sample comprising chromatin; (b) reacting the sample with a nicking enzyme, a polymerase and a labeled nucleotide to selectively label the open chromatin in the sample; and (c) analyzing the labeled sample of (b), wherein the analyzing is done by: (i) detecting an optically-detectable signal from the sample, if the labeled nucleotide comprises an optically detectable label; or (ii) enriching for and then sequencing fragments that comprise the labeled nucleotide, if the labeled nucleotide comprises an affinity tag.

Embodiment 15. The method of embodiment 14, wherein the labeled nucleotide comprises an optically detectable label and the analyzing step of (c) is performed by microscopy to produce an image of at least part of the sample.

Embodiment 16. The method of embodiment 14, wherein the labeled nucleotide comprises an affinity tag and the analyzing step of (c) is performed by: i. fragmenting the DNA in the sample, ii. enriching for fragments that contain the labeled nucleotide and iii. sequencing the enriched fragments.

Embodiment 17. The method of any of embodiments 14-17, wherein the sample comprises an isolated nucleus, and the chromatin is contained within an isolated nucleus.

Embodiment 18. The method of any of embodiments 14-17, wherein the composition comprises a permeabilized cell, wherein the chromatin is contained in the permeabilized cell.

Embodiment 19. The method of embodiment 18, wherein the cell is a fixed cell.

Embodiment 20. The method of embodiment 18, wherein the cell is an unfixed cell.

Embodiment 21. The method of any of embodiments 14-20, wherein the composition comprises a clinical sample, wherein the cell is in the clinical sample.

Embodiment 22. The method of embodiment 21, wherein the clinical sample is a tumor biopsy.

Embodiment 23. The method of any prior method embodiment, wherein the nicking enzyme is methylation-sensitive.

Embodiment 24. The method of any prior method embodiment, wherein the nicking enzyme is methylation-dependent.

Embodiment 25. A composition comprising: a nicking enzyme, a polymerase and a labeled nucleotide, further comprising chromatin.

Embodiment 26. The composition of embodiment 25, wherein the chromatin comprises open chromatin and closed chromatin, and at least some of the open chromatin is labeled by the labeled nucleotide.

Embodiment 27. The composition of any of embodiments 25-26, wherein the composition comprises an isolated nucleus, and the chromatin is contained within an isolated nucleus.

Embodiment 28. The composition of any of embodiments 25-26, wherein the composition comprises a permeabilized cell, wherein the chromatin is contained in the permeabilized cell.

Embodiment 29. The composition of embodiment 28, wherein the cell is a fixed cell or an unfixed cell.

Embodiment 30. The composition of any of embodiments 28-29, wherein the composition comprises a clinical sample, wherein the cell is in the clinical sample.

Embodiment 31. The composition of any of embodiments 25-30, wherein the labeled nucleotide comprises a detectable label.

Embodiment 32. The composition of any of embodiments 25-30, wherein the labeled nucleotide comprises an affinity tag.

Embodiment 33. The composition of any of embodiments 25-32, wherein the nicking enzyme is methylation-dependent.

Embodiment 34. The composition of any prior embodiment, wherein the nicking enzyme is methylation-sensitive.

Embodiment 35. A method for detecting open chromatin, further comprising reacting a sample comprising chromatin, wherein the chromatin comprises open chromatin, with a nicking enzyme, a polymerase, and a labeled nucleotide, to selectively label the open chromatin; and analyzing the labeled sample, wherein the analyzing is done by: (i) detecting an optically-detectable signal from the sample, if the labeled nucleotide comprises an optically detectable label; or (ii) enriching for and then sequencing fragments that comprise the labeled nucleotide, if the labeled nucleotide comprises an affinity tag.

Embodiment 36. A method for analyzing chromatin, comprising: reacting a sample comprising chromatin, wherein the chromatin comprises closed chromatin, with a methylation-dependent nicking enzyme, a polymerase, and a labeled nucleotide, to selectively label the closed chromatin; and analyzing the labeled sample, wherein the analyzing is done by: (i) detecting an optically-detectable signal from the sample, if the labeled nucleotide comprises an optically detectable label; or (ii) enriching for and then sequencing fragments that comprise the labeled nucleotide, if the labeled nucleotide comprises an affinity tag.

Embodiment 37. The method of embodiment 36, wherein the nicking enzyme nicks at methylated CpGs.

Embodiment 38. The method of any of embodiments 35-37, wherein the labeled nucleotide comprises an optically detectable label and the analyzing step of (c) is performed by microscopy to produce an image of at least part of the sample.

Embodiment 39. The method of any of embodiments 35-37, wherein the labeled nucleotide comprises an affinity tag and the analyzing step of (c) is performed by: i. fragmenting the DNA in the sample, ii. enriching for fragments that contain the labeled nucleotide and iii. sequencing the enriched fragments.

Embodiment 40. The method of any of embodiments 35-39, wherein the sample comprises an isolated nucleus, and the chromatin is contained within an isolated nucleus or wherein the composition comprises a permeabilized cell, wherein the chromatin is contained in the permeabilized cell.

Embodiment 41. A kit, comprising: a nicking enzyme, four dNTPs, and at least one labeled dNTP and a polymerase in a single reaction vessel or in a plurality of reaction vessels.

All publications, patents, and patent applications mentioned in this specification are herein incorporated by reference to the same extent as if each individual publication, patent, or patent application was specifically and individually indicated to be incorporated by reference. This includes U.S. Provisional Application 62/383,151 filed Sep. 2, 2016.

EXAMPLES

Aspects of the present teachings can be further understood in light of the following examples, which should not be construed as limiting the scope of the present teachings in any way.

MATERIALS AND METHODS

Cell culture: HCT116 cells were cultured in McCoy's 5A media supplemented with 10% fetal bovine serum.

Open chromatin labeling of fixed cells: One million HCT116 cells were used for routine library construction. Cells were cross-linked using 1% formaldehyde for 10 minutes at room temperature and quenched by using 125 mM glycine. Nuclei were isolated by incubating the cross-linked cells in cytosolic buffer (15 mM Tris-HCl pH 7.5, 5 mM $MgCl_2$, 60 mM KCl, 0.5 mM DTT, 15 mM NaCl, 300 mM sucrose and 1% NP40) for 10 minutes on ice with occasional agitation. Nuclei were precipitated by spinning at 1000×g, 4° C. for 5 minutes and supernatant were discarded. Open chromatin DNA was labeled with biotin by incubating the nuclei in presence of 2.5 U of Nt.CviPII, 50 U of DNA polymerase I and 30 µM of each dNTP including 6 µM of biotin-14-dATP (Invitrogen, Carlsbad, CA) and 6 µM of biotin-16-dCTP (ChemCyte, San Diego, CA) in 200 µL of 1×NEBuffer 2 (New England Biolabs, Ipswich, MA). The labeling reaction was carried out at 37° C. in a thermo-mixer for 2 hours. 20 µL of 0.5 M EDTA and 2 µg of RNase A was added to the labeling reaction and incubated at 37° C. for 0.5 hour to stop the labeling reaction and digest RNA.

Open chromatin labeling of unfixed cells: Open chromatin labeling on native/unfixed cells is exemplified here using freshly harvested HCT116 cells. Nuclei were isolated by incubating the cells in cytosolic buffer (15 mM Tris-HCl pH 7.5, 5 mM MgCl2, 60 mM KCl, 0.5 mM DTT, 15 mM NaCl, 300 mM sucrose, and 1% NP40) for 10 minutes on ice. Nuclei were precipitated by spinning at 1000×g, 4° C. for 5 minutes and the supernatant was discarded. Open chromatin DNA was labeled with biotin by incubating the nuclei in the presence of 2.5 U of Nt.CviPII, 10 U of DNA polymerase I and 30 µM of each dNTP including 6 µM of biotin-14-dATP and 6 µM of biotin-16-dCTP in 200 µL of 1×NEBuffer 2. The labeling reaction was carried out at 37° C. in a thermo-mixer at 800 RPM for 2 hours. Further, 20 µL of 0.5 M EDTA and 2 µg of RNase A to the labeling reaction and incubated at 37° C. for 0.5 hours to stop the reaction and digest RNA. Finally, 20 µL of proteinase K (New England Biolabs, Ipswich, MA) and 20 µL of 20% SDS was added to the reaction and incubated overnight at 65° C. Biotin-labeled genomic DNA was extracted using phenol chloroform.

Quantification of labeling efficiency-dot blot: Open chromatin labeling efficiency was analyzed by dot blot on genomic DNA. Genomic DNA purified from labeled chromatin was denatured by heating at 95° C. for 3 minutes followed by incubating in ice-water bath for 3 minutes. A serial dilution of genomic DNA was spotted onto positively charged nylon membrane (Roche, Basel, Switzerland) and cross-linked by UV.

Membrane was blocked by 5% non-fat milk and blotted using an HRP-conjugated goat anti-biotin antibody (1:2000 dilution, Cell Signaling Technology, Beverly, MA). Biotin signal was revealed using the LumiGLO® reagent (Cell Signaling Technology, Beverly MA). The above steps are embodiments of the method shown in FIG. 2.

Sequence Analysis of labeled chromatin: Subsequent to the labeling step described above, DNA-protein cross-linking was reversed by adding 20 µL of proteinase K and 20 µL of 20% SDS to the reaction and incubating at 65° C. for 1 hour. Biotin labeled genomic DNA was extracted using the phenol chloroform method. Labeling of open chromatin in unfixed cells was performed following the same method except for formaldehyde crosslinking step.

The genomic DNA was sonicated into 150 bp fragments (Covaris, Woburn, MA) and 1 µg of DNA was end-repaired, dA-tailed and ligated with NEBNext® Illumina adaptor (New England Biolabs, Ipswich, MA). Without further purification, the ligation product was mixed with 50 µL of Streptavidin magnetic beads ((Invitrogen, Carlsbad, CA), blocked using 0.1% cold fish gelatin in 1×PBS overnight at 4° C.) in 1 mL of B&W buffer (10 mM Tris-HCl pH 8.0, 1 mM EDTA, 2 M NaCl). Biotin-labeled open chromatin DNA was captured by streptavidin at 4° C. for 2 hours with end-over-end rotation. The beads were washed four times with B&W buffer plus 0.005% of Triton X-100 followed by one time wash with TE plus Triton X-100. The beads were resuspended in 40 µL of nuclease free water and 4 µL was used for library amplification using PCR. 10 PCR cycles were usually sufficient to generate enough amount of library DNA for sequencing.

For library construction using low amount of input cells (250 cells in this study), all procedures were the same as regular library construction except that 10 µg of glycogen was used during genomic DNA extraction to facilitate precipitation, and the entire extracted genomic DNA was used for sonication, 10 µL of streptavidin beads were used to capture the biotinylated DNA and all of the beads were used as template for library amplification. The above steps are embodiments of the method shown in FIG. 3.

Reads mapping and open chromatin peak calling: Adaptor and low quality sequences were trimmed from paired-end sequencing reads using Trim Galore with default settings (as found at the babraham.ac.uk website). Sequencing reads were mapped to reference human genome hg19 with Bowtie2 (Langmead, et al. Nat Methods 2012, 9:357-359). MACS2 was used with --broad --broad-cutoff 0.1 to call the peaks. The input library was generated using sonicated genomic DNA of normal HCT116 cells (Zhang, et al. Genome Biol 2008, 9:R137).

Association analysis of Nicking enzyme site density and open chromatin tag enrichment: To exclude the possibility that open chromatin DNA enrichment is solely caused by the occurrence of Nt.CviPII sites (CCD, D=A or G or T) in certain genomic regions but not the accessibility of chromatin by labeling enzymes, correlation analysis was performed on CCD site density and open chromatin tag density in 100-bp genomic tiles or open chromatin peak regions called by MACS2. Hg19 was scanned for Nt.CviPII sites and the genomic coordinates of Nt.CviPII sites were recorded. Nt.CviPII site density was expressed as sites per kb genomic sequence. Pearson linear correlation was implemented on the number of Nt.CviPII sites and the number of sequencing tags or Nt.CviPII site density and log 2 fold enrichment of open chromatin tags in MACS2 peak regions. The Pearson product-moment correlation coefficient was used to measure the degree of correlation (see FIG. 4A-4D).

Biotin-labeled genomic DNA from 25, 250, 2500, 25,000 and 250,000 cells were analyzed using the methods described above and the results are shown in FIG. 5A-5C and Table 3. Biotin-labeled genomic DNA from fixed and unfixed cells were analyzed using the methods described above. In order to make the comparison of NE-seq data using different amount of input cells, the mapped reads was normalized to 14.4 million mapped read pairs. Peaks were called using the same parameter with MACS2 as mentioned above (see FIG. 5A-5C and Table 3).

Analysis of association between open chromatin, histone modifications, transcription factor binding and CpG methylation status: Open chromatin peaks identified in NE-seq were correlated with H3K4me1, H3K4me3, H3K27ac, RNA pol II, and YY1. ChIP-seq sequencing reads of the HCT116 cell line were downloaded from the ENCODE project (wgEncodeEH002874, wgEncodeEH000949, wgEncodeEH002873, wgEncodeEH001627, and wgEncodeEH001671). Sequencing tag density of chromatin and transcription factor marks on open chromatin peaks was counted using HOMER (Heinz, et al. Mol Cell 2010, 38:576-589), and heat maps were plotted using the pheatmap package in R (Kolde R.: pheatmap: Pretty Heatmaps. 2015). When plotting tag densities of multiple data sets in the same heat map, peaks were sorted in descendent order based on the tag density of open chromatin. For the association analysis of CpG methylation and open chromatin, whole genome bisulfite sequencing data of the HCT116 cell line were retrieved from GEO (GSM1465024), CpG sites were mapped to the ±3 kb region of open chromatin and methylation ratio of single CpG sites were plotted on a heat map (see FIG. 6).

Genomic DNA from fixed (HCT116 and MCF7) and unfixed (HCT116) reactions were analyzed. The results are shown in FIG. 7A-7D.

Comparison of nicking enzyme with other chromatin profiling methods: The present method was compared with DNase I hypersensitivity sequencing (DNase-seq) in terms of sensitivity and specificity. DNase-seq data was downloaded from ENCODE (wgEncodeUw DnaseHct116AlnRep1, wgEncodeUwDnaseMcf7AlnRep1) (Meyer, et al. Nat Rev Genet 2014, 15:709-721). Sequencing reads were mapped and open chromatin peaks were called using MACS2 with the same parameters as the NE-seq experiment. Overlapped open chromatin peaks in both methods were identified using DiffBind package in R (Ross-Innes, et al. Nature 2012, 481:389-393). Distribution of the peaks was visualized using IGV browser. For a more detailed comparison between NE-seq and DNase-seq, the distribution of peaks across the genomes along with the common peaks was plotted as a bar graph (see FIG. 8A-8C).

Open chromatin labeling efficiency was analyzed by imaging labeled cells: Open chromatin labeling for the purpose of microscopy was performed by, culturing HeLa cells in an 8 well Lab-Tek II chambered coverglass system (Nalge Nunc International, Penfield, NY). The cells were fixed using 1% paraformaldehyde for 10 minutes and then washed thrice with 1×PBS for 5 minutes. Following this the fixed cells were incubated with cytosolic buffer for 10 minutes. Nicking reaction mix as described earlier was added to the cells with one change. Biotinylated dATP and dCTP were replaced by Texas Red-5-dATP and Texas Red-5-dCTP. The reaction was carried out for 1 hour and then the reaction was stopped by washing the cells with 1×PBS supplemented with 50 mM EDTA and 0.1% TritonX-100 (wash buffer) for 5 minutes. Nuclear staining was performed by incubating the cells in 1×PBS with 0.01% Hoechst stain for 5 minutes. Finally, cells were washed thrice with wash buffer for 10 minutes and visualized using a Zeiss LSM880 confocal microscope with 20× objective. The above steps are embodiments of the method shown in FIG. 9. Results obtained for Hela cells are shown in FIG. 10.

Labeling of open chromatin sites in fresh frozen tumor and normal tissue sections: Frozen tissue sections of various tumor biopsies were fixed using ice-cold acetone/methanol at −20° C. for 8 minutes and air-dried for 20 minutes. Dried sections were hydrated using 1×PBS for 5 minutes followed by immersion in cytosol extraction buffer (15 mM Tris, pH 7.5, 5 mM MgCl2, 60 mM KCl, 0.5 mM DTT, 15 mM NaCL, 300 mM sucrose, 1% NP40) for 10 minutes at room temperature. Labeling mix was added to the sections and incubated at 37° C. for 45 minutes. Labeling reaction was stopped by incubating the section in stop solution for 5 minutes and followed by 3 washes of 1×PBS with 0.05% TritonX-100 for 10 minutes each. Further sections were dehydrated in 70% and 100% ethanol washes for 2 minutes each; air-dried and mounted using DAPI containing mounting media. Finally, sections were visualized under a microscope for determining labeling efficiency. The visualization results for breast cancer tissue and adjacent no-cancerous tissue is shown in FIGS. 11A-13.

Calculation of open chromatin index (OCI) by image analysis: For imaging of the labeled sections, Texas Red-5-dATP and DAPI were detected using HeNe 633 laser and 405 laser respectively and visualized using a LSM880 confocal microscope. Using the histogram tool included in ZEN software the fluorescence intensity of the pixels from both red (Texas Red-5-dATP) and blue (DAPI) channels was determined. OCI was determined by calculating the ratio of red pixel intensity to blue pixel intensity. Box plot was plotted to visualize the OCI values for normal adjacent tissue and tumor tissue sections. Two-tailed student T-test was performed to determine the significance of the difference in OCI values.

Open chromatin labeling for NGS library preparation: Open chromatin labeling of fresh frozen tissue sections for matched adjacent normal tissue, tumor tissue, and tumor microarray was performed using 10 µm tissue sections mounted on glass slide with OCT. The specimen was fixed using cold acetone at −20° C. for 8 minutes in a coplin jar and air dried under a fume hood for 20 minutes. Following this the specimen was hydrated in 1×PBS for 5 minutes and incubated in cytosol extraction buffer for 10 minutes using a coplin jar. The boundary of the specimen was marked using a hydrophobic pen and chromatin labeling mix as described above under the section entitled "Open chromatin labeling of fixed cells". The dNTP mix was supplemented with biotin dATP and dCTP instead of Texas Red-5-dATP and dCTP. Following the labeling reaction, tissue specimen was scrapped off from the slide using fresh blade for each sample and processed for genomic DNA extraction using QIAamp® DNA mini kit (Qiagen, Hilden, Germany) as per the manufacturers protocol. NE-seq library from biotin-labeled genomic DNA was prepared using standard techniques for library preparation (New England Biolabs, Ipswich, MA)

Chromatin labeling using methylation specific nicking enzymes: HeLa cells were cultured in an 8 well Lab-Tek II chambered coverglass system. The cells were fixed using 1% paraformaldehyde for 10 minutes and then washed thrice with 1×PBS for 5 minutes. Following this the fixed cells were incubated with cytosolic buffer for 10 minutes. Nicking reaction mix as described earlier was added to the cells with one change. Biotinylated dATP and dCTP were replaced by Texas Red-5-dATP and Texas Red-5-dCTP. The reaction was carried out for 1 hour and then the reaction was stopped by washing the cells with 1×PBS supplemented with 50 mM EDTA and 0.1% TritonX-100 (wash buffer) for 5 minutes. Nuclear staining was performed by incubating the cells in 1×PBS with 0.01% Hoechst stain for 5 minutes. Finally, cells were washed thrice with wash buffer for 10 minutes and visualized using a Zeiss LSM 880 confocal microscope with 20× objective (Zeiss, Oberkochen, Germany).

Separation of human genome from unmethylated DNA using 5-methycytosine recognizing nicking enzymes: a mixture of human (Hela) genomic DNA and 100 bp unmethylated DNA ladder (New England Biolabs, Ipswich, MA) were combined and 5-methylcytosine specific nicking enzyme (1 ug of purified protein) was added along with 10 units of DNA pol I, 30 µM of dTTP and dGTP, 24 µM of dCTP and dATP along with 6 µM of biotinylated-dATP and -dCTP for 1 hour at 37° C. For streptavidin capture, 5 µl of streptavidin-magnetic beads were added and incubated for 2 hours at room temperature to capture methylated human gDNA (bound fraction). The remaining DNA in the supernatant was the unbound DNA/fraction. Once the supernatant was collected, the beads were washed using wash buffer (10 mM tris pH 8.0, 2 M NaCl, 1 mM EDTA). The DNA was resolved on 0.8% TBE agarose gel (see FIG. 20)

RESULTS

Nicking Enzyme Mediated Tagging of the Open Chromatin Regions

Nuclei from colorectal cancer HCT116 cells were incubated with Nt.CviPII nicking enzyme, that frequently nicks the human genomic DNA with sequence specificity CCD (D=A/G/T).

Using the method illustrated in FIG. 2A, either unfixed or formaldehyde fixed cell nuclei were incubated in buffer containing 2.5 units of Nt.CviPII for 1 hour at 37° C. The nicked open chromatin regions were filled-in using E. coli DNA polymerase I plus dNTP mixtures that were supplemented with biotin-14-dATP and biotin-16-dCTP to generate biotin-tagged open chromatin regions. To validate biotinylated chromatin, DNA was extracted, dot blotted and probed with anti-biotin antibody (FIG. 2B). Thus, both unfixed chromatin and formaldehyde fixed chromatin were efficiently labeled with biotin demonstrating that the nicking enzyme and E. coli DNA polymerase I were able to access the open chromatin in the nucleus.

Open Chromatin Enrichment is not Highly Associated with Nt.CviPII Density in the Genome It was demonstrated that Nt.CviPII recognition sequence density does not influence open chromatin enrichment by plotting nicking site density vs. log 2 fold enrichment of tags. A poor correlation in 100-bp genomic tiles was observed (FIG. 4A). A similar poor correlation was observed between number of nicking sites and sequence tags in the open chromatin peaks (FIG. 4B). These results demonstrate that the frequency of nicking sites has little bearing on open chromatin enrichment, and that the accessibility of the open chromatin to the nicking enzyme is the major determinant of tag reads. The sequences in the tag reads were identified as open chromatin site (OCS) (FIGS. 4C and 4D).

Open Chromatin Mapping with 25 Cells

The genomic DNA from the labeling reaction was purified, fragmented and captured using Streptavidin beads for library construction using the method illustrated in FIG. 3. Streptavidin-captured DNA from putative open chromatin regions was used for high throughput sequencing. To determine the robustness of NE-seq, we also used different amounts of fixed cells ranging from 25 to 250000. Numbers of discovered peaks between 2500 to 250000 cells did not drop significantly, but a 20% decrease occurred with 25 cells compared to 250 (Table 3). The overlapped peaks between 250-250,000 cells were in the range between 55%-72% suggesting a good correlation (FIG. 5A). Taken together, both peak numbers and overlaps, the lower limit for open chromatin mapping using NE-seq was determined to be ~25 cells. The OCS between 25-25000 cells was compared using selected genic regions and observed consistent tag density over 419 to 14 kb regions (FIGS. 5C and 5D), confirming the versatility of NE-seq.

NE-Seq and Distribution of Open Chromatin Sites in Cancer Cells

Heat maps for sequence reads obtained from NE-seq revealed the distribution of open chromatin in the genome. ENCODE datasets for various active chromatin marks and DNA-binding protein factors were confirmed using OCSs identified by NE-seq. The distribution of tag densities for various ChIP-seq experiments (H3K4me1, H3K4me3, H3K27ac, RNA pol II and YY1) in a ±3 kb window around the OCSs identified in NE-seq generated heat maps (FIG. 6). Heat map of NE-seq matched well with RNA pol II suggesting that most of the OCSs were bound with RNA pol II and are transcriptionally active. Furthermore, signature transcriptional activation marks H3K27ac and H3K4me3, also displayed strong enrichment around OCSs in the heat map. Also, H3K4me1, which is mainly enriched in the enhancer regions, were more depleted in the center and showed a bimodal distribution around OCS (FIG. 6). The heat map for CpG methylation status for OCSs inversely mirrored the NE-seq open chromatin configuration.

NE-Seq Identifies Unique and Divergent Peaks on Unfixed or Fixed Chromatin

Open chromatin configurations are preserved between unfixed and formaldehyde fixed cells. NE-seq of both HCT116 fixed and unfixed cells revealed that most of the open chromatin peaks in unfixed cells were a subset of the fixed cells where unfixed cell chromatin structure is likely to be dynamic and less efficient at incorporation of biotinylated dNTP (FIG. 7A). Sequence read peaks confirmed that some peaks or OCS were relatively static and the others were dynamic (FIG. 7B).

A comparison between OCS of MCF7 and HCT116 cells, showed an overlap of 24K peaks. This indicated the presence of both common and unique OCS specific to the cell type (FIG. 7C). Genome browser tracks also demonstrated both constitutive as well as unique OCS in MCF7 cells (FIG. 7D). Bar graph showing the peak distribution across different genomic regions revealed differential enrichment profiles (FIG. 7E).

NE-Seq and DNase-Seq Identify an Overlapping as Well as Unique Set of Open Chromatin Sites in Cancer Cells DNase-seq and NE-seq identify regions of chromatin devoid of nucleosomes and other DNA binding proteins. To quantify the level of overlap between these assays, we identified the peaks common to both techniques. ENCODE data for DNase-seq analysis of HCT116 cells was used to call peaks as described in materials and methods. Among 85K and 90K peaks identified by both NE-seq and DNase-seq respectively, 75% of them overlapped and ~25% were unique (FIG. 8A). Comparison of genome browser track profiles for OCS and DHS from both NE-seq and DNase-seq also displayed common peaks (FIG. 8B). Annotation of peaks unique to NE-seq, DNase-seq and common to both NE-seq and DNase-seq showed similar enrichment across different genomic regions (FIG. 8C).

Open Chromatin Labeling in Cultured Cells Using Enzyme Mixture and Labeled Colored Nucleotides Embodiments of the method described herein to identify tumor cells in a biopsy and to differentiate these cells from non-tumor cells can be used in the context of any method capable of introducing a foreign nucleotide into open chromatin. For example, any of the prior art methods described in Table 1 including ATAC-seq that relies on the use of transposons may be used in the present method for identifying tumor cells.

As described above and as shown in FIG. 9, Texas Red-5-dATP can be used to fill in the cross-linked HeLa cells after the nicking enzyme incubation to demonstrate the labeling of OCS. Indeed, the cells without Nt.CviPII and E. coli DNA polymerase I (control) displayed no Texas Red signal (FIG. 10A). Strong labeling was observed when Nt.CviPII, E. coli DNA polymerase I and Texas Red-5-dATP and Texas Red-5-dCTP were added to cells (FIG. 10A). The cells were scored for Texas Red-5-dATP/dCTP incorporation and compared to DAPI for OCI measurement (FIG. 10B). Thus, cross-linked cells were efficiently labeled and the labeling reaction could be visualized in the nucleus.

Method Validation of Open Chromatin Labeling in Patient Biopsy Sections

Fresh frozen acetone fixed breast cancer tissue sections were used to access open chromatin labeling and OCI calculation. Texas Red-5-dATP was used to fill in the cross-linked tissue sections after the nicking enzyme incubation to demonstrate the labeling of OCS. The cells were scored for Texas Red-5-dATP/dCTP incorporation and compared to DAPI for OCI measurement. Indeed, the sections without Nt.CviPII and E. coli DNA polymerase I (control) or E. coli DNA polymerase I plus Texas Red-5-dATP displayed no fluorescence signal (FIG. 11A). Only in the presence of Nt.CviPII, E. coli DNA polymerase I and Texas Red-5-dATP/dCTP we observed fluorescence signal confirming open chromatin labeling (FIG. 11A). Box plot of OCI values showing the quantitation of open chromatin was plotted (FIG. 11B).

Open Chromatin Labeling in Patient Biopsy Sections Using Enzyme Mixture and Texas Red-5-dATP Open chromatin labeling in fresh frozen acetone fixed Her2+ normal adjacent breast tissue section was performed using dNTPs supplemented with Texas Red-5-dATP/dCTP, Nt.CviPII, and E. coli DNA polymerase I.

Labeling reactions were performed in the absence of Nt.CviPII and DNA polymerase I showed background levels of fluorescence incorporation (FIG. 12, top panel). Further, labeling reaction performed in the presence of Nt.CviPII and DNA polymerase I showed limited levels of OCS labeling (FIG. 12, bottom panel). Herceptin levels were determined using anti-her2 antibody. Her2 levels were close to background as expected for a normal breast tissue section.

In another experiment, open chromatin was labeled in fresh frozen acetone fixed Her2+ breast cancer tissue section using enzyme mix and Texas Red-5-dATP/dCTP. As expected, labeling reaction performed in the absence of Nt.CviPII and DNA polymerase I showed background levels of fluorescence (FIG. 13, top panel). Further, labeling reaction performed in the presence of Nt.CviPII and DNA polymerase I showed robust labeling (FIG. 13, bottom panel). High levels of Her2+ cells as expected were identified in the tumor tissue. Interestingly, all the cells labeled with Texas Red-5-dATP/dCTP were also identified as Her2+ cancerous cells. Merging of Her2, Texas Red-5-dATP/dCTP and DAPI images clearly revealed the architecture of an invasive ductile carcinoma as observed by strong and high density staining of the nucleus and the cell surface. Boxplot showing the labeling efficiency of OCSs was plotted revealing strong increase in OCI for tumor vs normal adjacent tissue with a p value of 3.6e-9 (FIG. 14). This demonstrated higher OCI index in invasive ductile carcinoma compared to adjacent normal tissue.

Six additional cancer types including lung, pancreas, stomach, colon, bladder and liver cancer were similarly tested and the results are summarized in FIG. 15. FIG. 15 provides an OCS index and available epidemiological data. In all the cancer types tested a significantly higher OCS index was observed for tumor sections when compared to normal adjacent tissue sections. Further, the increase in OCI for tumor sections was highly significant with p values ranging from $e^{-4}$ to $e^{-9}$ for all tested tissue sections.

When DNase I hypersensitive sites (DHS) and OCS reads were compared for HCT116 cells, about a third of them from either method remain unique. Further transcriptional and histone marks analysis and comparison of these unique sequence tags revealed that the OCS peaks are more enriched for modified histones—H3K4me3 and H3K27ac. This demonstrates that non-random nicking enzymes provide higher specificity than random nicking enzymes resulting in more accurate open-chromatin region determination. Furthermore, OCS between two different cancer cell lines demonstrated cell type specific and common open chromatin regions suggesting conservation of OCS in mammalian cells.

Methylated Chromatin Labeling Using 5-Methycytosine Recognizing Nicking Enzymes.

Formaldehyde fixed cells were incubated with a nicking enzyme: NhoI, BisI or Pam 79021 (all of which nick genomic duplex DNA when one or two $^mCpGs$ are present in their DNA recognition sequences) DNA PolI and Texas Red conjugated dATP using methods described above. The nuclei of the human HeLa cell line were labeled as illustrated in FIG. 19, column 1. A merge between nuclear DAPI staining and Texas Red-5-dATP stained cells are shown in column 3. All three nicking enzymes were able to recognize and nick the methylated chromatin as shown with Texas Red in FIG. 19. Alternatively, use of biotin labeled dNTPs would enable capture of methylated chromatin for sequencing.

Separation and Enrichment of Human Genome from Unmethylated DNA Using 5-Methycytosine Recognizing Nicking Enzymes.

In a mixture of human genomic DNA that is naturally CpG methylated ($^{5m}CpG$) and unmethylated synthetic DNA, the human genomic DNA was shown to be selectively nicked and labeled with Biotinylated-dATP and Biotinylated-dCTP by a $^{5m}C$ recognizing nicking enzymes and a suitable DNA polymerase, as described herein. This reaction was incubated with streptavidin magnetic beads for human genomic DNA binding. The bound fraction was observed to retain all detectable human DNA whereas the unbound fraction contained the unmethylated DNA as shown on the gel in FIG. 20.

TABLE 1

Comparison of NE-seq with other methods

| No. of Cells | Mnase-seq 1 to 10 Million | Dnase-seq 1 to 10 Million | FAIRE-seq 100,00 to 10 Million | ATAC-seq 500-50,000 | NE-seq 25-250,000 |
|---|---|---|---|---|---|
| Sequencing type | Paired-end or Single-end | Paired-end or Single-end | Paired-end or Single-end | Paired-end | Paired-end or Single-end |
| Genomic target | MNase digested unprotected genomic DNA | DNase I cut unprotected genomic DNA | phenol-chloroform separation of nucleosome-bound and free sonicated areas of a genome | Unfixed nuclei tagged in vitro with adapters for NGS by purified Tn5 transposase | Native or Fixed nuclei Enzyme accessible genomic DNA |

TABLE 1-continued

Comparison of NE-seq with other methods

| No. of Cells | Mnase-seq 1 to 10 Million | Dnase-seq 1 to 10 Million | FAIRE-seq 100,00 to 10 Million | ATAC-seq 500-50,000 | NE-seq 25-250,000 |
|---|---|---|---|---|---|
| Read out | Total nucleosome population in a qualitative and quantitative manner | Maps open chromatin | Maps open chromatin | Maps open chromatin, TF and nucleosome occupancy | Maps open chromatin, TF and nucleosome occupancy |
| Drawbacks | Requires many cells | Requires many cellsextensive enzyme titration | Low signal-to-noise ratio, making computational data interpretation very difficult | Contamination of generated data with mitochondrial DNA Requires 60 to 100 million reads for standard accessibility studies of the human genome | |

TABLE 2

Open chromatin indexing in cancer

| Tissue | Grade | ANT-OCI | Tumor-OCI | p value |
|---|---|---|---|---|
| Breast (BB) | pT2 N1a MX | 0.15 | 1.35 | $3.6E^{-6}$ |
| Lung (USB) | ‖ | 0.6 | 3.0 | $1.67E^{-6}$ |
| Pancreas (BB) | pT1c N0 M0 | 0.76 | 2.45 | $1.03E^{-5}$ |
| Stomach (BB) | pT3 N0 MX | 2.1 | 8.3 | $4E^{-4}$ |
| Colon (BB) | pT3 N0 Mx | 0.96 | 11.85 | $2.5E^{-7}$ |
| Bladder (BB) | pT3b N0 MX | 4.6 | 9.7 | $7E^{-4}$ |
| Kidney (BB) | pT3b NX MX | 5.9 | 7.3 | 0.05 |
| Liver (BB) | pT1 N0 MX | 2.5 | 6.55 | $4E^{-4}$ |
| Vulva (USB) | I | 0.05 | 0.19 | $2E^{-6}$ |
| Ovary (USB) | I | 0.08 | 0.6 | $5.5E^{-10}$ |
| Thyroid gland (USB) | NA | 0.09 | 0.35 | $3.24E^{-12}$ |
| Skeletal muscle (USB) | NA | 0.07 | 0.6 | $6.2E^{-14}$ |

ANT - Adjacent Normal Tissue
OCI - Open Chromatin Index
pT - Primary tumor
N - Status of metastasis to regional lymph nodes
M - Distant metastasis

TABLE 3 shows the number of total mapped reads and the number of peaks identified before and after normalizing the total mapped reads to the level of 25 HCT116 cells.

| Number of cells | Total mapped read pairs | Number of peaks discovered | Number of peaks discovered using same number of mapped reads |
|---|---|---|---|
| 25 | 14761229 | 10569 | 10569 |
| 250 | 14386139 | 65308 | 65308 |
| 2,500 | 22562588 | 97244 | 78728 |
| 25,000 | 21021107 | 106274 | 86822 |
| 250,000 | 24616388 | 87276 | 83899 |

NE-seq is a straightforward method that can be performed on potentially any cell type from any species with a sequenced genome. It has similar but better resolution to DNase-seq and no prior knowledge is required with regards to histone modifications, transcription factor binding sites, gene annotation, or relative degree of sequence conservation between species. It can identify the location of most active gene regulatory elements with no false positive reads. This will aid in understanding chromatin landscape during mammalian development and epigenetic drug discovery.

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

What is claimed is:

1. A method for detecting abnormal cells in or from a tissue section or biopsy wherein the abnormal cells have altered chromatin compared to normal cells, comprising:
   (a) reacting the cells with a composition comprising a mixture of a nicking enzyme, four dNTPs, and at least one labeled dNTP, and a polymerase to selectively label the chromatin;
   (b) incorporating the labeled dNTP into the chromatin of the cells to form labelled nucleic acid; and
   (c) analyzing the pattern of labelled nucleic acid in the cells.

2. The method according to claim 1, wherein (c) further comprises determining whether the pattern of labelled nucleic acid corresponds to a cancer diagnosis of the cells or tissues.

3. The method according to claim 1, wherein prior to (a), making the cells permeable.

4. The method according to claim 1, wherein the tissue section or biopsy is fixed.

5. The method according to claim 3, wherein the tissue section or biopsy is fixed.

6. The method according to claim 1, wherein after (b) reverse cross linking and isolating DNA from the cells.

7. The method according to claim 1, wherein following (b), labelling nuclei from the cells with a primary antibody.

8. The method according to claim 7, wherein after labelling with a primary antibody, labelling with a secondary antibody.

9. The method according to claim 7, further comprising: visualizing the labelled nuclei using a fluorescent microscope.

* * * * *